United States Patent
Clark

(10) Patent No.: US 10,197,392 B2
(45) Date of Patent: Feb. 5, 2019

(54) AUTOMATED RESIN RIDGE REDUCTION SYSTEM

(71) Applicant: The Boeing Company, Chicago, IL (US)

(72) Inventor: Gregory L. Clark, Issaquah, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/747,222

(22) Filed: Jun. 23, 2015

(65) Prior Publication Data

US 2016/0377424 A1  Dec. 29, 2016

(51) Int. Cl.
| | | |
|---|---|---|
| *G01B 11/30* | (2006.01) | |
| *G01M 17/007* | (2006.01) | |
| *G05D 1/00* | (2006.01) | |
| *G01N 21/95* | (2006.01) | |
| *G01N 21/84* | (2006.01) | |

(52) U.S. Cl.
CPC ......... *G01B 11/303* (2013.01); *G01M 17/007* (2013.01); *G01N 21/9515* (2013.01); *G05D 1/0088* (2013.01); *G01N 2021/8472* (2013.01); *G01N 2021/9518* (2013.01)

(58) Field of Classification Search
CPC .............. G01B 11/30; G01N 29/265; G01N 2021/8472; G05D 1/0088
USPC .......................................................... 356/600
See application file for complete search history.

(56) References Cited

U.S. PATENT DOCUMENTS

| | | | | | |
|---|---|---|---|---|---|
| 3,636,635 | A | * | 1/1972 | Lemelson | G01B 7/008 33/505 |
| 4,509,369 | A | * | 4/1985 | Kuljis | G01N 29/221 376/249 |
| 5,031,458 | A | * | 7/1991 | Young | G01N 29/265 73/618 |
| 5,117,169 | A | * | 5/1992 | Kakino | G05B 19/401 318/570 |
| 5,317,387 | A | * | 5/1994 | Van Hengel | G01N 21/88 356/446 |
| 5,468,099 | A | * | 11/1995 | Wheetley | B23B 39/04 180/8.1 |
| 6,829,959 | B2 | * | 12/2004 | Gifford | G01N 27/902 73/577 |
| 6,871,684 | B2 | * | 3/2005 | Engelbart | G01N 21/88 156/361 |
| 6,964,312 | B2 | * | 11/2005 | Maggio | B62D 49/0635 15/340.1 |
| 7,039,485 | B2 | * | 5/2006 | Engelbart | B29C 70/386 156/379 |
| 7,253,908 | B2 | * | 8/2007 | Vaccaro | G01B 11/24 356/607 |

(Continued)

OTHER PUBLICATIONS

Extended European Search Report, dated Oct. 25, 2016, regarding Application No. EP16173389.4, 6 pages.

*Primary Examiner* — Roy M Punnoose
(74) *Attorney, Agent, or Firm* — Yee & Associates, P.C.

(57) ABSTRACT

An apparatus comprises an automated guided vehicle that moves on a surface of a composite structure during operation of the apparatus to inspect the composite structure, a surface inspection sensor system associated with the automated guided vehicle, and an automated guided vehicle and surface inspection sensor system controller in communication with the automated guided vehicle and the surface inspection sensor system.

1 Claim, 17 Drawing Sheets

(56) References Cited

U.S. PATENT DOCUMENTS

| | | | |
|---|---|---|---|
| 7,289,656 B2* | 10/2007 | Engelbart | G01N 21/95 382/141 |
| 7,444,876 B2* | 11/2008 | Sarr | G01N 29/226 73/618 |
| 7,464,596 B2* | 12/2008 | Bui | G01N 29/043 73/618 |
| 7,467,052 B2* | 12/2008 | Vaccaro | G01N 29/0636 702/66 |
| 7,769,224 B2* | 8/2010 | Engelbart | G01N 21/95 382/141 |
| 7,832,030 B2* | 11/2010 | Nunez | A46B 11/00 4/300 |
| 8,016,970 B2 | 9/2011 | Dull et al. | |
| 8,019,472 B2* | 9/2011 | Montero SanJuan | B21J 15/14 180/8.1 |
| 8,220,991 B2 | 7/2012 | Safai et al. | |
| 8,281,442 B2* | 10/2012 | Eggleston | B08B 1/02 15/21.1 |
| 8,514,412 B2* | 8/2013 | Bennison | G01B 11/14 356/626 |
| 9,193,402 B2* | 11/2015 | Chin | G05D 1/0246 |
| 9,221,506 B1* | 12/2015 | Georgeson | B05C 1/00 |
| 9,250,213 B1* | 2/2016 | Bossi | G01N 29/265 |
| 9,302,787 B2* | 4/2016 | Hafenrichter | B64F 5/0018 |
| 9,334,066 B2* | 5/2016 | Tapia | B64F 5/0045 |
| 9,475,527 B2* | 10/2016 | Gamboa | B62D 57/024 |
| 9,481,082 B1* | 11/2016 | Hafenrichter | B25J 5/02 |
| 9,545,697 B2* | 1/2017 | Whinnem | B23Q 1/5462 |
| 2003/0048081 A1* | 3/2003 | Seemann | B62D 55/00 318/68 |
| 2006/0017937 A1* | 1/2006 | Vaccaro | G01B 11/24 356/607 |
| 2006/0043303 A1 | 3/2006 | Safai | |
| 2012/0300221 A1* | 11/2012 | Bennison | G01B 11/14 356/601 |
| 2013/0018525 A1 | 1/2013 | Jang et al. | |
| 2013/0024067 A1* | 1/2013 | Troy | B25J 5/007 701/36 |
| 2013/0234030 A1* | 9/2013 | Shelley, Jr. | G01N 21/8806 250/353 |
| 2014/0182479 A1* | 7/2014 | Hafenrichter | B64F 5/0018 105/30 |
| 2014/0210946 A1* | 7/2014 | Hsiao | H04N 13/0214 348/46 |
| 2014/0210997 A1 | 7/2014 | Blanchard et al. | |
| 2014/0305216 A1* | 10/2014 | Hafenrichter | G01N 29/07 73/598 |
| 2014/0305217 A1* | 10/2014 | Tapia | B64F 5/0045 73/618 |
| 2014/0305220 A1 | 10/2014 | Fetzer et al. | |
| 2015/0003927 A1* | 1/2015 | Spishak | B25J 5/007 408/1 R |
| 2015/0135459 A1* | 5/2015 | Lee | B08B 7/04 15/246 |
| 2016/0026176 A1* | 1/2016 | Leggett | G06F 1/1613 700/110 |
| 2016/0146741 A1* | 5/2016 | Shelley, Jr. | G01N 21/94 356/237.3 |

* cited by examiner

AUTOMATED RESIN RIDGE REDUCTION SYSTEM

BACKGROUND INFORMATION

1. Field

The present disclosure relates generally to composite structures and, in particular, to composite structures for vehicles. Still more particularly, the present disclosure relates to a method and apparatus of inspecting and reducing resin ridges on composite structures for aircraft.

2. Background

In manufacturing composite wings for aircraft, caul plates may be used to reduce the effects of crenulations from laying up tape and fabric. Caul plates may also be used to smooth out transition areas.

These caul plates, however, may cause ridges to form along the edges of the caul plates. Inspections may be performed to identify ridges that may have a size that is greater than desired. Other operations that may cause undesired resin ridges include bagging creases and transition areas between co-bonded and co-cured parts. Further, reworking or discarding composite structures may increase the cost in manufacturing aircraft by an undesirable amount.

Therefore, it would be desirable to have a method and apparatus that take into account at least some of the issues discussed above, as well as other possible issues. For example, without limitation, it would be desirable to have a method and apparatus that take into account the technical problem with the increased time, increased expense, safety issues, ergonomic issues or some combination thereof with reworking or discarding composite structures.

SUMMARY

An embodiment of the present disclosure may provide an apparatus comprising an automated guided vehicle that moves on a surface of a composite structure during operation of the apparatus to inspect the composite structure, a surface inspection sensor system associated with the automated guided vehicle, and the automated guided vehicle and surface inspection sensor system controller in communication with the automated guided vehicle and the surface inspection sensor system.

Another embodiment of the present disclosure provides a method for reducing an inconsistency on a surface of a composite structure. An automated guided vehicle may be automatically moved to a location on the surface of the composite structure. Inspection information about the surface of the composite structure at the location may be automatically generated with a surface inspection sensor system. An inconsistency that is out of tolerance on the surface of the composite structure at the location may be automatically scanned for using the inspection information, enabling an efficient reduction of the inconsistency.

Yet another embodiment of the present disclosure may comprise a resin reduction system comprising an automated guided vehicle that may move on a surface of a composite structure during operation of the resin reduction system to inspect the composite structure, a surface inspection sensor system associated with the automated guided vehicle, an inconsistency reduction system associated with the automated guided vehicle, and the automated guided vehicle and surface inspection sensor system controller in communication with the automated guided vehicle and the surface inspection sensor system. The surface inspection sensor system may generate inspection information about the surface of the composite structure during the operation of the resin reduction system. The automated guided vehicle and the surface inspection sensor system controller, during the operation of the resin reduction system, may autonomously control movement of the automated guided vehicle on the surface of the composite structure; may receive the inspection information from the surface inspection sensor system; may identify a measured profile from the inspection information; may compare the measured profile with an expected profile to form a comparison; may determine whether the inconsistency is out of tolerance and should be reduced based on the comparison; may identify how much to reduce the inconsistency from the comparison when the inconsistency is out of tolerance and should be reduced; and may control the inconsistency reduction system to reduce the inconsistency that is identified as being out of tolerance. The controller may then tag a location of the inconsistency when the inconsistency should not be reduced to be within tolerance by performing at least one of physically marking the location with a material, storing coordinates of the location, or storing directions to the location, enabling an efficient reduction of the inconsistency.

Still another embodiment of the present disclosure may comprise a method for reducing resin on a surface of a composite structure. A location for an inspection may be identified by detecting at least one of a pen mark, paint, a sticker, tape, a landmark, a structure, a radio frequency identifier chip, a stringer, or a rib at the location on the surface of the composite structure. An automated guided vehicle may be automatically moved to the location on the surface of the composite structure. The automated guided vehicle moves over the surface of the composite structure by at least one of moving over the surface without contact with the surface or moving over the surface while in contact with the surface. The automated guided vehicle may be selected from one of an autonomous crawler, an aerial drone, an unmanned ground vehicle, and an unmanned aerial vehicle. A controller may autonomously control movement of the automated guided vehicle on the surface of the composite structure. Inspection information about the surface of the composite structure at the location may be automatically generated with a sensor system. The sensor system may be selected from at least one of a near infrared imaging camera, a laser scanner, a visible light camera, a stereoscopic camera, a tactile sensor system, a physical probe, a micrometrology probe, a chromatic white light sensor, or a video camera. The method automatically may scan for an inconsistency that is out of tolerance on the surface of the composite structure at the location using the inspection information by identifying a measured profile from the inspection information. The measured profile may be compared with an expected profile to form a comparison. The method may determine whether the inconsistency is out of tolerance and should be reduced based on the comparison. Further, the method may identify how much to reduce the inconsistency from the comparison when the inconsistency is out of tolerance and should be reduced. The size of the inconsistency may be reduced with an inconsistency reduction system when the inconsistency is out of tolerance until the inconsistency is within tolerance, enabling an efficient reduction of the undesired inconsistency. The inconsistency reduction system may be selected from at least one of a sanding device, a ridge reduction system, a laser reduction system, an end effector, or a laser system. The location may automatically be tagged when the inconsistency should not be reduced to be within a tolerance by performing at least one of physically marking the location with a material, storing coordinates of the location, or storing directions to the location. Location information about a current location of at least one of the automated guided vehicle or a group of automated guided vehicles may automatically be generated. The movement of the automated guided vehicle on the surface may be controlled using the location information received from the sensor system.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, without limitation, the illustrative embodiments recognize and take into account that in manufacturing composite wings for aircraft, caul plates used to reduce the effects of crenulations from laying up tape and fabric and smooth out transition areas may result in ridges formed of resin. The illustrative embodiments recognize and take into account these types of ridges may be reduced in size through operations such as sanding the resin ridges.

Currently, with the concern of sanding into fibers, human operators may inspect the wing for defects and perform sanding by hand. In some cases, the human operators may use a sanding tool such as a pneumatic tool with a rotary grinding attachment. This type of process for removing excess resin may be very labor-intensive. Additionally, the illustrative embodiments recognize and take into account that in reducing resin, sanding into fibers in the wing may be undesirable. Over sanding may result in an increased amount of rework or discarding of the composite wing.

The illustrative embodiments recognize and take into account that composite cured parts may be subject to the occurrence of inconsistencies from impacts to the composite cured parts. This type of inconsistency may be referred to as barely visible impact damage (BVID). The illustrative embodiments recognize and take into account that manual work performed on a cured composite part may be a source of this type of inconsistency.

The illustrative embodiments also recognize and take into account that having human operators move on a wing and perform inspections and sanding may have ergonomic issues as well as potentially causing additional undesired inconsistencies on the wing. As a result, the illustrative embodiments recognize and take into account that manufacturing composite wings, as well as other composite structures for aircraft, may be more time-consuming and costly than desired with the currently used processes for removing resin from the surfaces of composite structures.

Thus, the illustrative embodiments provide a method and apparatus for reducing inconsistencies on a surface of a composite part. For example, without limitation, a process may be implemented that reduces an undesired inconsistency on a surface of a composite structure. An automated guided vehicle (AGV) may be automatically moved to a location on the surface of the composite structure. Inspection information may be automatically generated about the surface of the composite structure at the location with a sensor system. The method may automatically scan for an inconsistency that is out of tolerance on the surface of the composite structure at the location using the inspection information, enabling an efficient reduction of the undesired inconsistency.

Figure 1:
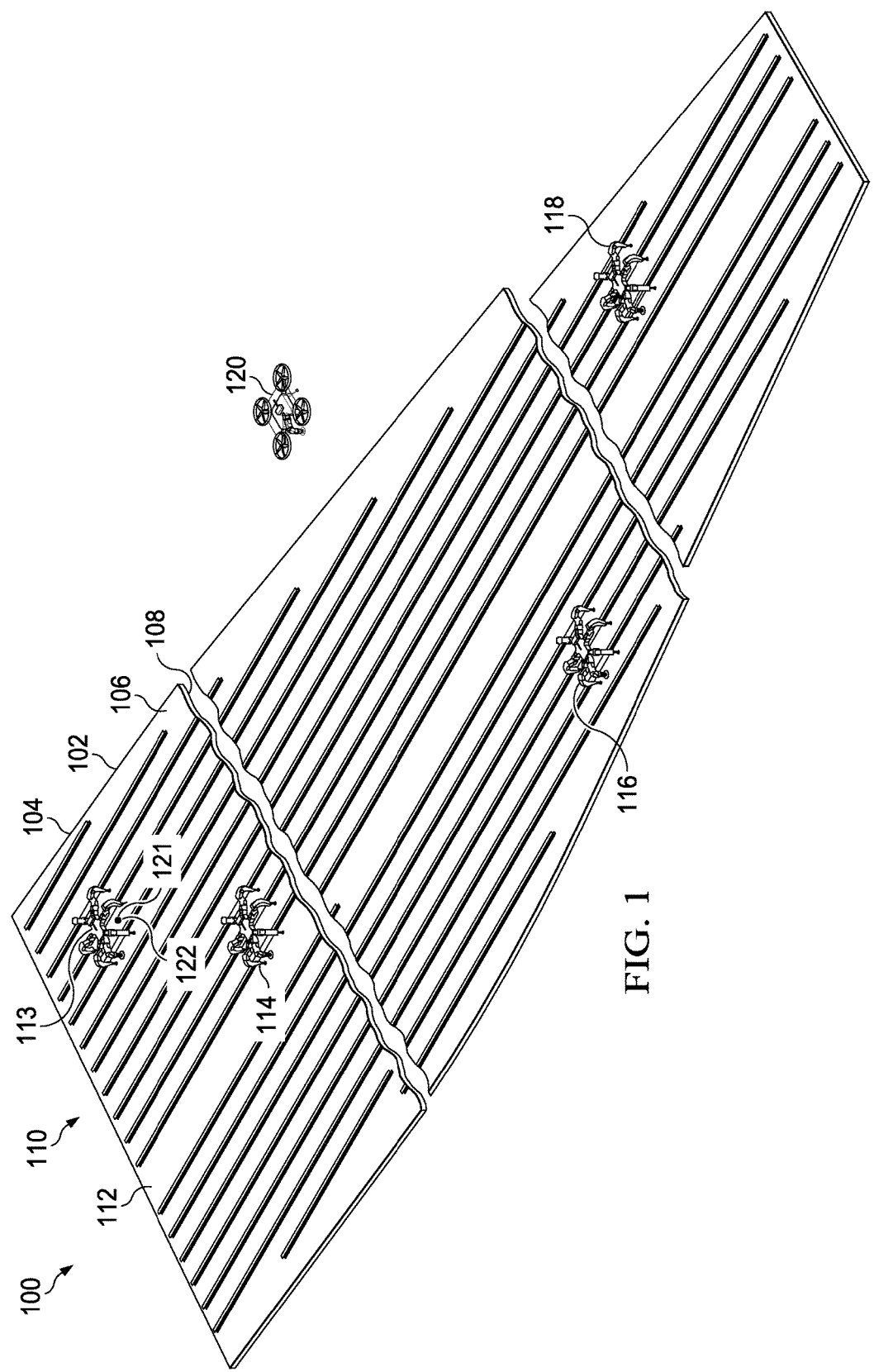
FIG. 1 is an illustration of a composite manufacturing environment in accordance with an illustrative embodiment.

With reference now to the figures and, in particular, with reference to FIG. 1, an illustration of a composite manufacturing environment is depicted in accordance with an illustrative embodiment. In this illustrative example, composite manufacturing environment 100 may include wing 102. As depicted, wing 102 may be composite wing 104 for an aircraft. Wing 102 may have inner mold line 106 and outer mold line 108.

As depicted, mobile inspection units 110 may move on surface 112 of inner mold line 106 on wing 102. In this illustrative example, mobile inspection units 110 include crawler 113, crawler 114, crawler 116, crawler 118, and aerial drone 120.

In this illustrative example, mobile inspection units 110 may move on surface 112 and inspect surface 112. For example, without limitation, when inconsistency 121 in the form of resin ridge 122 is located by crawler 113, crawler 113 may determine whether inconsistency 121 may be changed from being out of tolerance to being within tolerance. Crawler 113 may determine whether resin ridge 122 may be reduced in size through sanding without reaching fibers (not shown) in wing 102.

If resin ridge 122 may be reduced in size without sanding into fibers (not shown) in wing 102, crawler 113 may perform a sanding operation to reduce resin ridge 122. Otherwise, crawler 113 may mark resin ridge 122 for later review or analysis.

In this illustrative example, a portion of mobile inspection units 110 may be configured to locate inconsistencies on wing 102 that are out of tolerance. Another portion of mobile inspection units 110 may move to those locations and perform rework such that the inconsistencies located on wing 102 become within tolerance.

Figure 2:
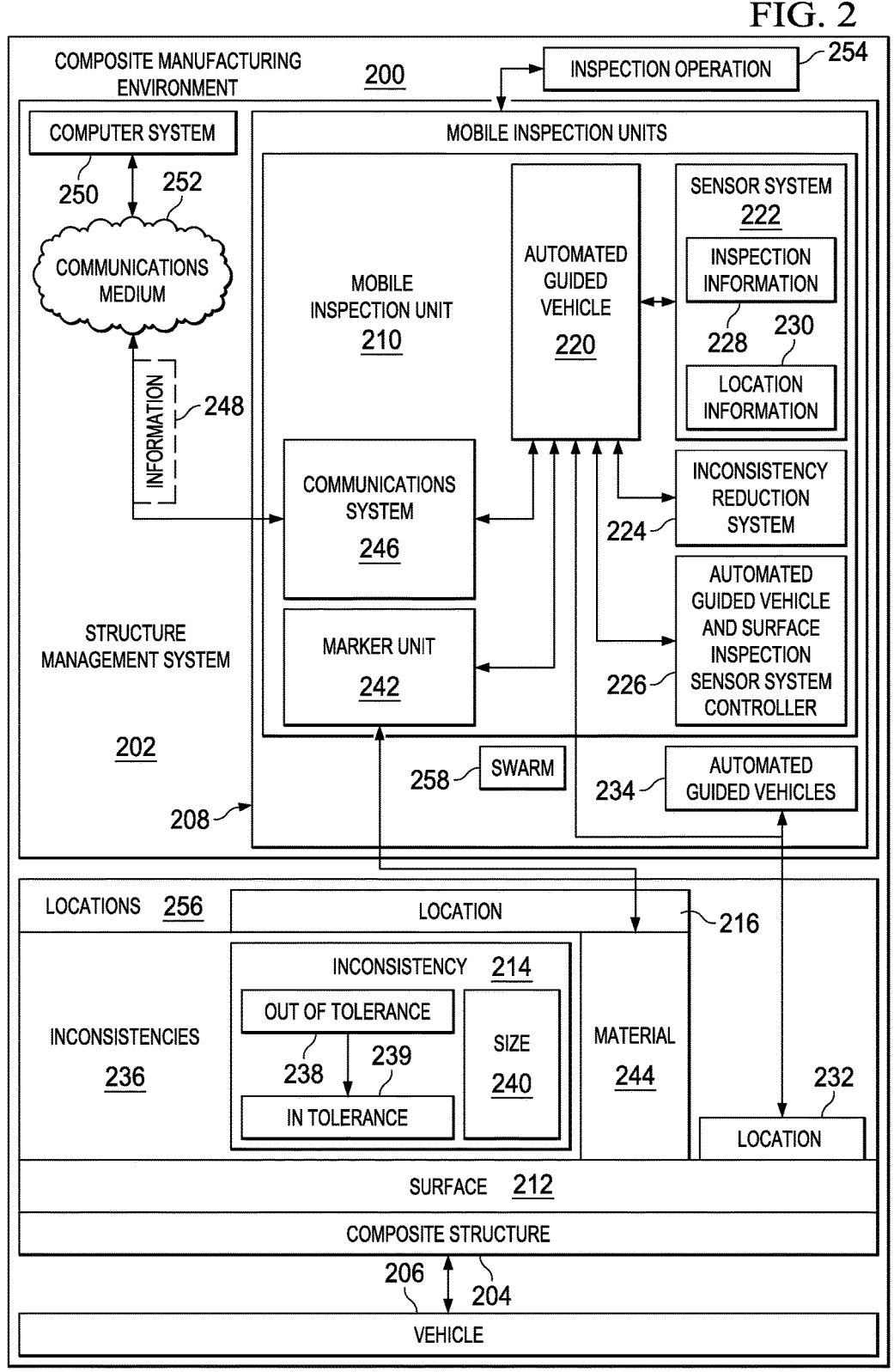
FIG. 2 is an illustration of a block diagram of a composite manufacturing environment in accordance with an illustrative embodiment.

Turning next to FIG. 2, an illustration of a block diagram of a composite manufacturing environment is depicted in accordance with an illustrative embodiment. Composite manufacturing environment 100 in FIG. 1 may be an example of one implementation of composite manufacturing environment 200 shown in block form in FIG. 2.

As depicted, composite manufacturing environment 200 includes structure management system 202. Structure management system 202 may be used to inspect composite structure 204. In the illustrative example, composite structure 204 may take different forms. For example, without limitation, composite structure 204 may be selected from one of a vehicle part, an aircraft part, an aircraft, a wing, a fuselage section, an engine cowling, a horizontal stabilizer, a passenger cabin floor, a hood for an automobile, or some other suitable structure.

For example, without limitation, composite structure 204 may be for vehicle 206. Composite structure 204 may be partially manufactured or completed when inspected by structure management system 202. Further, composite structure 204 may be separate from vehicle 206 or may be installed in vehicle 206 when inspected by structure management system 202.

The inspection by structure management system 202 may be performed by a group of mobile inspection units 208. As used herein, "a group of," when used with reference to items, means one or more items. For example, without limitation, "a group of mobile inspection units 208" may be one or more of mobile inspection units 208.

In one illustrative example, mobile inspection unit 210 in mobile inspection units 208 may move on surface 212 of composite structure 204 during operation of mobile inspection unit 210 to inspect composite structure 204. As depicted, mobile inspection unit 210 may inspect surface 212 of composite structure 204 at location 216. In particular, mobile inspection unit 210 may search for inconsistency 214 on surface 212 of composite structure 204 at location 216.

In the illustrative example, location 216 may be a location on composite structure 204. For example, without limitation, location 216 may be a point or an area in this example. When location 216 is an area, the area may be a circle, a square, an oval, a quadrilateral, an irregular shape, or some other form.

In the illustrative example, mobile inspection unit 210 may be considered autonomous when mobile inspection unit 210 operates independently. For example, without limitation, mobile inspection unit 210 may be considered autonomous when mobile inspection unit 210 moves without commands or guidance from a human operator (not shown). As another example, mobile inspection unit 210 may be considered autonomous when mobile inspection unit 210 inspects surface 212 without commands or guidance from a human operator (not shown). For example, without limitation, mobile inspection unit 210 may be an autonomous crawler.

In this illustrative example, mobile inspection unit 210 may include a number of components. As depicted, mobile inspection unit 210 may include automated guided vehicle 220, sensor system 222, inconsistency reduction system 224, and automated guided vehicle and surface inspection sensor system controller 226.

Automated guided vehicle 220 may be a platform for the other components in mobile inspection unit 210. As depicted, automated guided vehicle 220 moves over surface 212 of composite structure 204 during operation of mobile inspection unit 210 to inspect composite structure 204. By moving over surface 212, automated guided vehicle 220 may be in contact with surface 212, above surface 212 and out of contact with surface 212, or some combination thereof. As depicted, automated guided vehicle 220 may move over surface 212 of composite structure 204 by at least one of moving over surface 212 without contact with surface 212 or moving over surface 212 while in contact with surface 212.

As used herein, the phrase "at least one of," when used with a list of items, means different combinations of one or more of the listed items may be used and only one of each item in the list may be needed. In other words, "at least one of" means any combination of items and number of items may be used from the list, but not all of the items in the list are required. The item may be a particular object, thing, or a category.

For example, without limitation, "at least one of item A, item B, or item C" may include item A, item A and item B, or item B. This example also may include item A, item B, and item C or item B and item C. Of course, any combinations of these items may be present. In some illustrative examples, "at least one of" may be, for example, without limitation, two of item A; one of item B; and ten of item C; four of item B and seven of item C; or other suitable combinations.

Automated guided vehicle 220 may move over surface 212 without contact with surface 212 when automated guided vehicle 220 is an aerial drone, an unmanned aerial vehicle, or some other suitable automated guided vehicle that moves in the air. Automated guided vehicle 220 may move over surface 212 with contact with surface 212 when automated guided vehicle 220 is an autonomous crawler, an unmanned ground vehicle, or some other suitable automated guided vehicle that has a locomotion system that moves with direct contact with surface 212. In yet another illustrative example, automated guided vehicle 220 may be a vehicle that moves on rails (not shown) that may be attached to composite structure 204.

Automated guided vehicle 220 may take different forms. For example, without limitation, automated guided vehicle 220 may be selected from one of a crawler, an autonomous crawler, an aerial drone, an unmanned ground vehicle (UGV), an unmanned aerial vehicle (UAV), or some other suitable type of platform.

In this illustrative example, sensor system 222 may be a hardware system. As depicted, sensor system 222 may be associated with automated guided vehicle 220. In the different examples, when one component is "associated" with another component, the association is a physical association in the depicted examples. For example, without limitation, a first component, sensor system 222, may be considered to be physically associated with a second component, automated guided vehicle 220, by at least one of being secured to the second component, bonded to the second component, mounted to the second component, welded to the second component, fastened to the second component, or connected to the second component in some other suitable manner. The first component also may be connected to the second component using a third component. The first component may also be considered to be physically associated with the second component by being formed as part of the second component, extension of the second component, or both.

Sensor system 222 may generate inspection information 228 about surface 212 of composite structure 204 during operation of mobile inspection unit 210. Sensor system 222 may be in communications with automated guided vehicle and surface inspection sensor system controller 226 and send inspection information 228 to automated guided vehicle and surface inspection sensor system controller 226.

Sensor system 222 also may be used to identify location 216 to perform inspection of surface 212. For example, without limitation, the identification of location 216 may be made by sensor system 222 detecting at least one of a pen mark, paint, a sticker, tape, a stringer, a rib, a structure, a radio frequency identifier (RFID) chip, or some other landmark or tag at or adjacent to location 216.

Sensor system 222 may generate location information 230 and send location information 230 to automated guided vehicle and surface inspection sensor system controller 226. Location information 230 may be used by automated guided vehicle and surface inspection sensor system controller 226 control movement of automated guided vehicle 220.

As depicted, sensor system 222 also may generate location information 230 about location 232 of at least one of automated guided vehicle 220 or a group of automated guided vehicles 234 for mobile inspection units 208. In this example, location 232 may be a current location for at least one of automated guided vehicle 220 or a group of automated guided vehicles 234 for mobile inspection units 208.

As depicted, sensor system 222 may be implemented using one or more devices or systems. For example, without limitation, sensor system 222 may be selected from at least one of a near infrared imaging camera, a laser scanner, a visible light camera, a stereoscopic camera, a tactile sensor system, a physical probe, a micrometrology probe, a chromatic white light sensor, a video camera, or some other suitable system. As used herein, a system may be formed from one or more devices.

In the illustrative example, inconsistency reduction system 224 may be a hardware system and may be associated with automated guided vehicle 220. Inconsistency reduction system 224 may reduce inconsistencies 236 on surface 212 of composite structure 204 that are out of tolerance 238. The reduction may be performed through at least one of sanding, grinding, abrasive reduction, laser ablation, plasma etching, or in some other suitable manner.

As depicted, tolerance 238 may be selected in a number different ways. For example, without limitation, tolerance 238 may be selected using design specifications, safety regulations, and other sources that may be provide guidance to select tolerance 238. For example, without limitation, the resin ridges may need to be less than about 0.003 inches in interface areas. As another example, the resin ridges may need to be less than about 0.01 inches in tooling areas and less than about 0.02 inches in bag side areas.

As depicted, inconsistency reduction system 224 may be selected from at least one of a sanding device, a ridge reduction system, a laser reduction system, an end effector, a laser system, an ablation system, a trimming system, a cutting system, or some other suitable system. In this example, automated guided vehicle and surface inspection sensor system controller 226 may be in communication with automated guided vehicle 220, sensor system 222, and inconsistency reduction system 224. Automated guided vehicle and surface inspection sensor system controller 226 may control operation of one or more of these components during operation of mobile inspection unit 210.

For example, without limitation, automated guided vehicle and surface inspection sensor system controller 226 may autonomously control movement of automated guided vehicle 220 on surface 212 of composite structure 204. Automated guided vehicle and surface inspection sensor system controller 226 may control movement of automated guided vehicle 220 using location information 230 received from sensor system 222.

During operation of mobile inspection unit 210, automated guided vehicle and surface inspection sensor system controller 226 may receive inspection information 228 from sensor system 222 and may determine whether inconsistency 214 that is out of tolerance 238 on surface 212 of composite structure 204 that can be reduced in a desired manner to be within tolerance 238 using inspection information 228. As depicted, inconsistency 214 may be out of tolerance 238 when size 240 of inconsistency 214 is greater than desired. Automated guided vehicle and surface inspection sensor system controller 226 may control inconsistency reduction system 224 to reduce size 240 of inconsistency 214 when inconsistency 214 can be reduced from being out of tolerance 238 to being within tolerance 239.

As depicted, automated guided vehicle and surface inspection sensor system controller 226 may be implemented in software, hardware, firmware or a combination thereof. When software is used, the operations performed by automated guided vehicle and surface inspection sensor system controller 226 may be implemented in program code configured to run on hardware, such as a processor unit. When firmware is used, the operations performed by automated guided vehicle and surface inspection sensor system controller 226 may be implemented in program code and data and stored in persistent memory to run on a processor unit. When hardware is employed, the hardware may include circuits that operate to perform the operations in automated guided vehicle and surface inspection sensor system controller 226.

In the illustrative examples, the hardware may take the form of a circuit system, an integrated circuit, an application-specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations. Programmable logic devices include, for example, without limitation, a programmable logic array, programmable array logic, a field programmable logic array, a field programmable gate array, and other suitable hardware devices. Additionally, the processes may be implemented in organic components integrated with inorganic components and may be comprised entirely of organic components excluding a human being. For example, without limitation, the processes may be implemented as circuits in organic semiconductors.

As depicted, automated guided vehicle and surface inspection sensor system controller 226 may have different levels of intelligence. For example, without limitation, automated guided vehicle and surface inspection sensor system controller 226 may include processes that allow mobile inspection unit 210 to operate autonomously. These processes may include at least one of an artificial intelligence (AI) process, a neural network, or other suitable processes.

In some cases, inconsistency 214 that is out of tolerance 238 should not be reduced to become within tolerance 238. For example, in some cases, reduction may result in fiber exposure of inconsistency 214. In the illustrative example, automated guided vehicle and surface inspection sensor system controller 226 may tag location 216 of inconsistency 214 when inconsistency 214 cannot be reduced to become within tolerance 238. In tagging location 216, automated guided vehicle and surface inspection sensor system controller 226 may perform at least one of physically marking location 216, storing coordinates of location 216, storing directions to location 216, or some other suitable operation to identify location 216.

For example, without limitation, mobile inspection unit 210 may also include marker unit 242. Marker unit 242 may be a physical device associated with automated guided vehicle 220 and may mark location 216.

For example, without limitation, automated guided vehicle and surface inspection sensor system controller 226 may control operation of marker unit 242 to mark surface 212 at location 216 with material 244. As depicted, material 244 may be selected from at least one of an ink, a tape, paint, a label, or other material for marking onto surface 212 at location 216. As a result, subsequent inspections may be performed to decide how to handle inconsistency 214 that is out of tolerance 238 when inconsistency 214 should not be reduced to be within tolerance 238.

In another example, mobile inspection unit 210 may include communications system 246 that may be associated with automated guided vehicle 220. Communications system 246 may facilitate the exchange of information 248 between mobile inspection unit 210 and computer system 250.

Computer system 250 may include one or more data processing systems. When more than one computer is present, those computers may communicate with each over a communications medium 252. Communications medium 252 may be a network with wired links, optical links, wireless links, or some combination thereof. The data processing systems may be selected from at least one of a computer, a server computer, a workstation, a tablet computer, a laptop computer, a mobile phone, or some other suitable data processing system.

As depicted, automated guided vehicle and surface inspection sensor system controller 226, sensor system 222, and inconsistency reduction system 224 may form a feedback loop. In the illustrative example, sensor system 222 may generate inspection information 228 used by automated guided vehicle and surface inspection sensor system controller 226 to control the operation of inconsistency reduction system 224. Automated guided vehicle and surface inspection sensor system controller 226 may control inconsistency reduction system 224 to reduce inconsistency 214 that is out of tolerance 238. Sensor system 222 may continue to generate inspection information 212 during the reduction of inconsistency 214 as feedback about the reduction of inconsistency 214. When inconsistency 214 is within tolerance 238, then automated guided vehicle and surface inspection sensor system controller 226 may control inconsistency reduction system 224 to halt reducing inconsistency 214.

Communications system 246 may be in communication with computer system 250 through communications medium 252. Information 248 exchanged may be selected from at least one of a task for mobile inspection unit 210, results of an inspection, indication of a location of inconsistency 214, images of location 216, a map of surface 212, coordinates to location 216, directions to location 216, or other suitable information.

Additionally, mobile inspection unit 210 may communicate with other ones of mobile inspection units 208. This communication may be through communications medium 252, directly between mobile inspection units 208, or some combination thereof. As depicted, mobile inspection units 208 may coordinate the performance of inspection operation 254 with each other.

This coordination may include a collective behavior where mobile inspection units 208 work together to inspect composite structure 204. This coordination may include mobile inspection units 208 dividing up or selecting locations 256 on surface 212 for inspection and inconsistency reduction. In this manner, mobile inspection units 208 may operate as swarm 258.

In this manner, inconsistency reduction system 224 with mobile inspection unit 210 enables an efficient reduction of inconsistency 214 in a manner that inconsistency 214 changes from being out of tolerance 238 to being within tolerance 238. When inconsistency 214 is a resin ridge, mobile inspection unit 210 may be a resin reduction system and, in particular, may be a resin ridge reduction system. As a result, one or more technical solutions may be present that solve the technical problem with the increased time, increased expense, or both the increased time and expense occurring with reworking or discarding composite structures.

Figure 3:
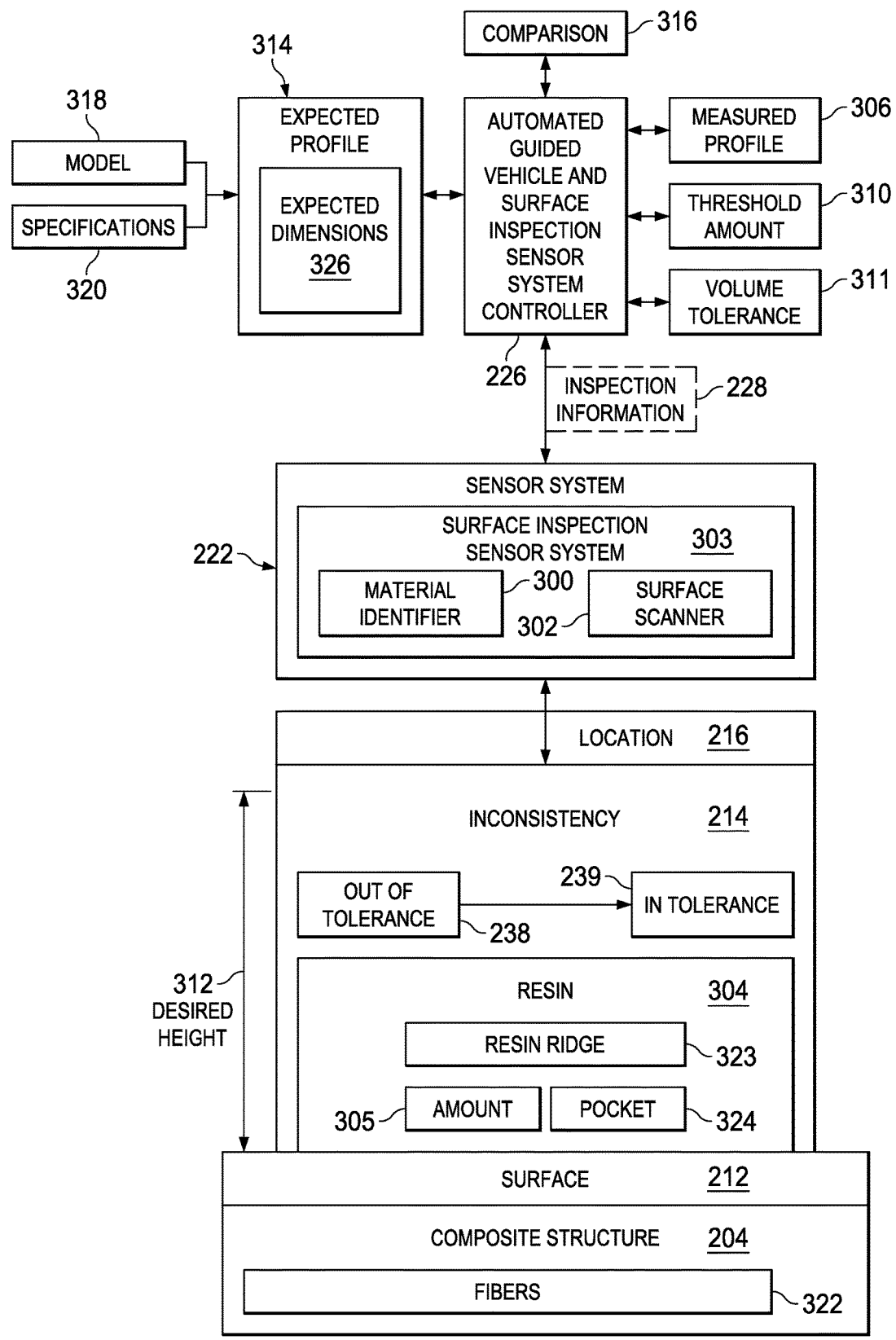
FIG. 3 is an illustration of data flow for detecting an undesired inconsistency in accordance with an illustrative embodiment.

With reference next to FIG. 3, an illustration of data flow for detecting an undesired inconsistency is depicted in accordance with an illustrative embodiment. In the illustrative examples, the same reference numeral may be used in more than one figure. This reuse of a reference numeral in different figures represents the same element in the different figures.

In this illustrative example, automated guided vehicle and surface inspection sensor system controller 226 receives inspection information 228 from sensor system 222 and uses inspection information 228 to determine whether inconsistency 214 is present on surface 212 of composite structure 204. For example, inspection information 228 may be used to determine whether inconsistency 214 is resin ridge 323. Inspection information 228 may also be used to identify other types of inconsistencies 236. For example, without limitation, inspection information 228 may be used identify foreign object damage (FOD), fibers 322 above surface 212, a wrinkle containing fibers, or other types of inconsistencies 236.

As depicted, sensor system 222 may include surface inspection sensor system 303. In this depicted example, material identifier 300 and surface scanner 302 form surface inspection sensor system 303. In this particular example, material identifier 300 may be configured to identify a presence of resin 304 in amount 305 that is greater than a desired amount. In other words, material identifier 300 may determine whether amount 305 of resin 304 in inconsistency 214 is out of tolerance 238.

Material identifier 300 may be configured to generate inspection information 228 that may be used to identify amount 305 of resin 304 that is present. Material identifier 300 may be, for example, without limitation, selected from at least one of an infrared camera, a near infrared (NIR) imaging camera, or some other suitable device.

As depicted, surface scanner 302 may be configured to generate inspection information 228 that includes or may be used by automated guided vehicle and surface inspection sensor system controller 226 to identify measured profile 306 for surface 212. Surface scanner 302 may be selected as at least one of a laser scanner, a physical probe, a micrometrology probe, a stereoscopic camera, or some other suitable device.

In the depicted example, surface scanner 302 may generate measured profile 306 and send measured profile 306 to automated guided vehicle and surface inspection sensor system controller 226 in inspection information 228. In another illustrative example, sensor system 222 may send inspection information 228, and automated guided vehicle and surface inspection sensor system controller 226 may generate measured profile 306 from inspection information 228.

A profile, such as measured profile 306, may be an outline or cross section of an object, such as composite structure 204, formed on a vertical plane through the object. The profile may be a single cross section or multiple cross sections that form a three-dimensional profile. For example, without limitation, measured profile 306 may be a contour map, a three-dimensional elevation profile, a three-dimensional surface map, or some other suitable indication of the dimensions of surface 212 at location 216.

As depicted, automated guided vehicle and surface inspection sensor system controller 226 may identify location 216 of resin 304 within inconsistency 214. In this particular illustrative example, automated guided vehicle and surface inspection sensor system controller 226 may be configured to locate resin 304 from inspection information 228 generated by material identifier 300 when amount 305 of resin 304 present is greater than threshold amount 310. As depicted, when amount 305 of resin 304 present is greater than threshold amount 310, resin 304 for may be considered out of tolerance 238.

Threshold amount 310 may be a level when resin 304 is considered to be resin rich at location 216. Resin 304 may be considered to be resin rich when amount 305 of resin 304 results in an undesired performance of composite structure 204, composite structure 204 not performing as well as desired, composite structure 204 does not perform at all, or some combination thereof. For example, resin 304 may be considered resin rich when the ratio of the volume of resin 304 to the volume of fibers 322 is higher than indicated volume tolerance 311.

As depicted, measured profile 306 may be used to determine whether resin 304 in inconsistency 214 is above desired height 312 for surface 212 or embedded under surface 212 below desired height 312 of composite structure 204 (not shown). For example, concern may be present with respect to protrusions, such as ridges, that may be higher than desired above the surface of the inner mold line, the outer mold line or both. Inconsistency 214 may result from different sources such as caul plates, bag pleats, protruding parts, combining parts, or other sources.

For example, without limitation, automated guided vehicle and surface inspection sensor system controller 226 may compare measured profile 306 to expected profile 314 to form comparison 316. In one illustrative example, measured profile 306 may be a measured or actual profile for surface 212, such as an inner mold line.

Expected profile 314 may be expected dimensions 317 for surface 212 at location 216. Expected profile 314 may be obtained in a number of different ways. For example, without limitation expected profile 314 may be a flat surface or a surface with a known curve. In another illustrative, expected profile 314 may be based on model 318. With comparison 316, a determination may be made as to whether surface 212 is above desired height 312.

In the illustrative example, surface 212 may also be lower than desired height 312. In this case, rework is not performed. Instead, surface 212 at location 216 may be tagged using marker unit 242 for an additional inspection.

In this illustrative example, expected profile 314 may be obtained from various sources. For example, without limitation, expected profile 314 may be obtained from at least one of model 318 of composite structure 204, specifications 320 for composite structure 204, or some other suitable source.

When resin 304 in inconsistency 214 is out of tolerance 238, inconsistency 214 may be above desired height 312. In this case, inconsistency 214 may be reduced to become within intolerance 238 if removing a portion or all of resin 304 avoids at least one of removing or exposing fibers 322 in composite structure 204. In other words, grinding or sanding of fibers 322 may be avoided when reducing inconsistency 214.

If resin 304 is below desired height 312, then resin 304 may not be resin ridge 323. Instead, resin 304 may be pocket 324 of resin 304. In this case, resin 304 may not be removed. When resin 304 is below desired height 312, a depression may be present and may be tagged using marker unit 242 for future disposition. These areas typically are not resin starved and may occur from a depression in a tool or a misalignment of plies.

Thus, automated guided vehicle and surface inspection sensor system controller 226 may determine whether resin 304 in inconsistency 214 is resin ridge 323 that is out of tolerance 238. Additionally, automated guided vehicle and surface inspection sensor system controller 226 may determine whether resin ridge 323 may be reduced to desired height 312 if resin ridge 323 is greater than desired height 312.

In the illustrative example, if inconsistency 214 is a ridge that is not resin rich, then the ridge may be a wrinkle in which fiber is present. When inconsistency 214 is resin rich in the form of resin ridge 323, fibers within resin ridge 323 are unlikely to be present.

As depicted, material identifier 300 determines whether inconsistency 214 is resin rich, while surface scanner 302 identifies the presence of a ridge. In this manner, automated guided vehicle and surface inspection sensor system controller 226 may control inconsistency reduction system 224 in a desired manner to reduce inconsistency 214 when resin ridge 323 is above desired height 312.

The illustrative example may provide a method and apparatus for reworking composite structure 204 in a manner that solves the technical problem with the increased time, increased expense, or both the increased time and expense occurring with reworking or discarding composite structures. As depicted, mobile inspection unit 210 may perform inspections and rework that reduces inconsistency 214. As depicted, the reduction may reduce inconsistency 214 that is out of tolerance 238 to become within intolerance 238. Further reductions in time, expense, or expense and time may occur when mobile inspection units 208 perform inspections on composite structure 204 cooperatively as swarm 258.

The illustration of composite manufacturing environment 200 and the different components in this environment in FIGS. 1-2 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, without limitation, other types of inspection units in addition to or in place of mobile inspection unit 210 may be used in structure management system 202. In one illustrative example, mobile inspection unit 210 may be one that is placed on surface 212 at the location of the inconsistency.

As another example, without limitation, controller 226 for mobile inspection unit 210 may or may not be physically associated with automated guided vehicle 220. Automated guided vehicle and surface inspection sensor system controller 226 may be located in a location selected from at least one of automated guided vehicle 220, another automated guided vehicle (not shown), or computer system 250.

Also, surface scanner 302 may send data in inspection information 228 that may be used by automated guided vehicle and surface inspection sensor system controller 226 to generate measured profile 306. In still another illustrative example, sensor system 222 may also include a camera that may be used to generate location information 230 that may be used to navigate on surface 212 of composite structure 204. In another illustrative example, sensor system 222 may include a global positioning system unit that generates location information 230.

In still another illustrative example, one portion of mobile inspection units 208 may be configured to inspect locations 256. Another portion of mobile inspection units 208 may be configured to arrive at locations 256 where inconsistencies 236 are found to be out of tolerance 238 to perform rework or other operations to bring in inconsistencies 236 into tolerance 238. The cooperative operations performed by mobile inspection units 208 may be performed as swarm 258.

Figure 4:
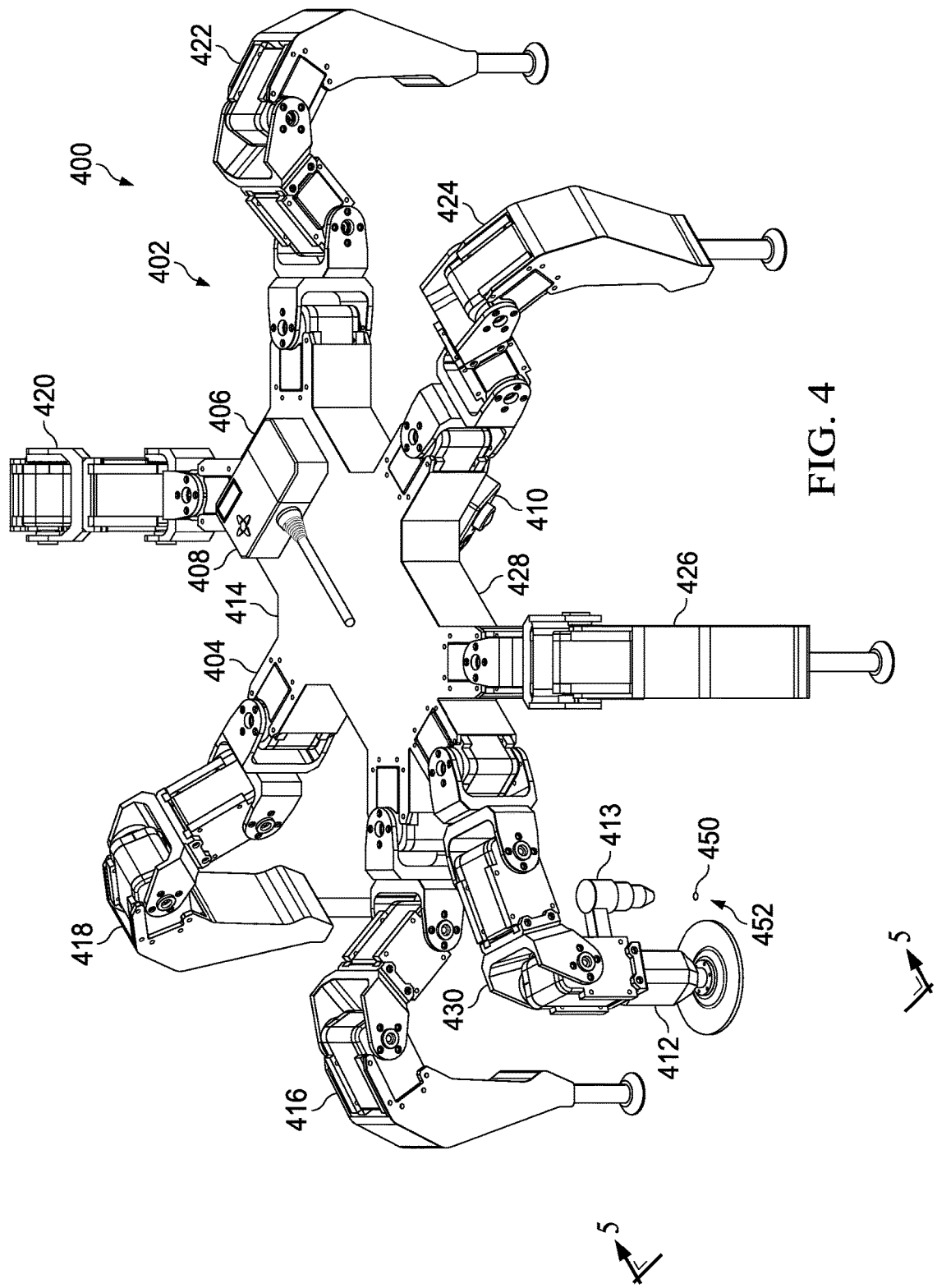
FIG. 4 is an illustration of a mobile inspection unit in accordance with an illustrative embodiment.

With reference now to FIG. 4, an illustration of a mobile inspection unit in the form of a crawler is depicted in accordance with an illustrative embodiment. Mobile inspection unit 400 may be crawler 402, such as crawler 113 in FIG. 1, in this example. As depicted, crawler 402 may be an example of a physical implementation for mobile inspection unit 210 shown in block form in FIG. 2.

As depicted in this view, crawler 402 may have a number of different components. For example, without limitation, crawler 402 may include automated guided vehicle 404, controller 406, communications system 408, laser scanner 410, grinder 412, and marker unit 413.

In this illustrative example, automated guided vehicle 404 may be crawler 402 in the form of hexapod 414. As depicted, hexapod 414 may have leg 416, leg 418, leg 420, leg 422, leg 424, and leg 426 that are associated with body 428. In this manner, crawler 402 may move by walking. As depicted, leg 416, leg 418, leg 420, leg 422, leg 424, and leg 426 help crawler 402 step over surface protrusions such as stringers (not shown). Further, crawler 402 also may be deployed before caul plates (not shown) are removed to inspect for ridges (not shown) between the caul plates.

Controller 406 may be associated with automated guided vehicle 404 and may be an example of a physical implementation of automated guided vehicle and surface inspection sensor system controller 226 shown in block form in FIG. 2. Controller 406 may be in communication with automated guided vehicle 404, communications system 408, laser scanner 410, grinder 412, and other components not shown in this view. Controller 406 may control the operation of these different components to perform inspection and rework of operations.

In this illustrative example, communications system 408 may be a wireless communication system. Communications system 408 may provide exchange of information with other devices such as, for example, without limitation, mobile inspection units 208 (not shown) and computer system 250 (not shown).

Laser scanner 410 may be an example of an implementation for surface scanner 302 shown in block form in FIG. 3. Grinder 412 may be physically associated with automated guided vehicle 404 through robotic arm 430. As depicted, grinder 412 may be an example of a physical implementation for inconsistency reduction system 224 shown in block form in FIG. 2.

As depicted, marker unit 413 may apply ink 450 to mark location 452 if needed. Ink 450 may flag location 452 for further inspection or analysis. In some implementations, marker unit 413 may be omitted.

Figure 5:
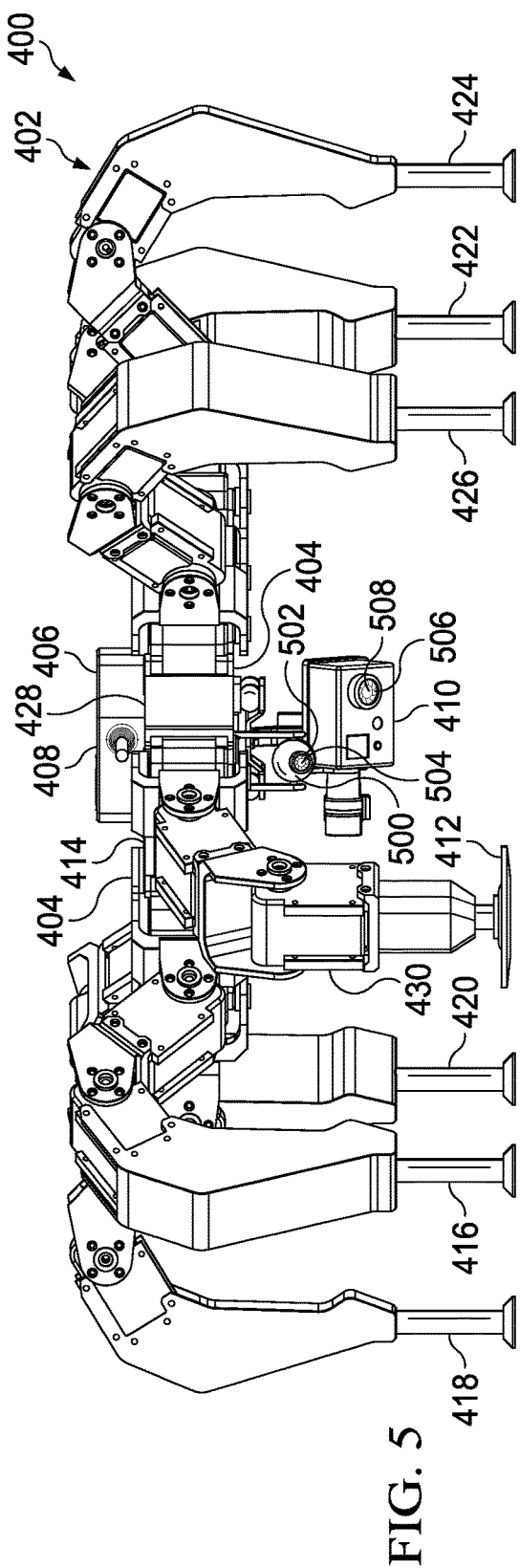
FIG. 5 is another illustration of a mobile inspection unit in accordance with an illustrative embodiment.

With reference next to FIG. 5, another illustration of mobile inspection unit 400 is depicted in accordance with an illustrative embodiment. In this figure, mobile inspection unit 400 is shown in a view in the direction of lines 5-5 in FIG. 4.

In this view of mobile inspection unit 400, near infrared (NIR) camera 500 may be seen associated with automated guided vehicle 404. Near infrared camera 500 may be an example of one implementation for material identifier 300 shown in block form in FIG. 3.

As depicted in this illustrative example, shutter 502 is seen in this view. Shutter 502 is associated with lens 504 on near infrared camera 500. Shutter 502 may operate to block dust (not shown) generated when grinding is performed using grinder 412. As another example, shutter 506 is associated with lens 508 on laser scanner 410. In a similar fashion, shutter 506 may protect lens 508 from dust build up (not shown) on lens 508 occurring during grinding. The dust generated from grinding may be cleaned up during other operations such as hole formation, trimming, or other suitable operations using other equipment when mobile inspection unit 400 is not operating or has been moved to another location or composite structure.

Figure 6:
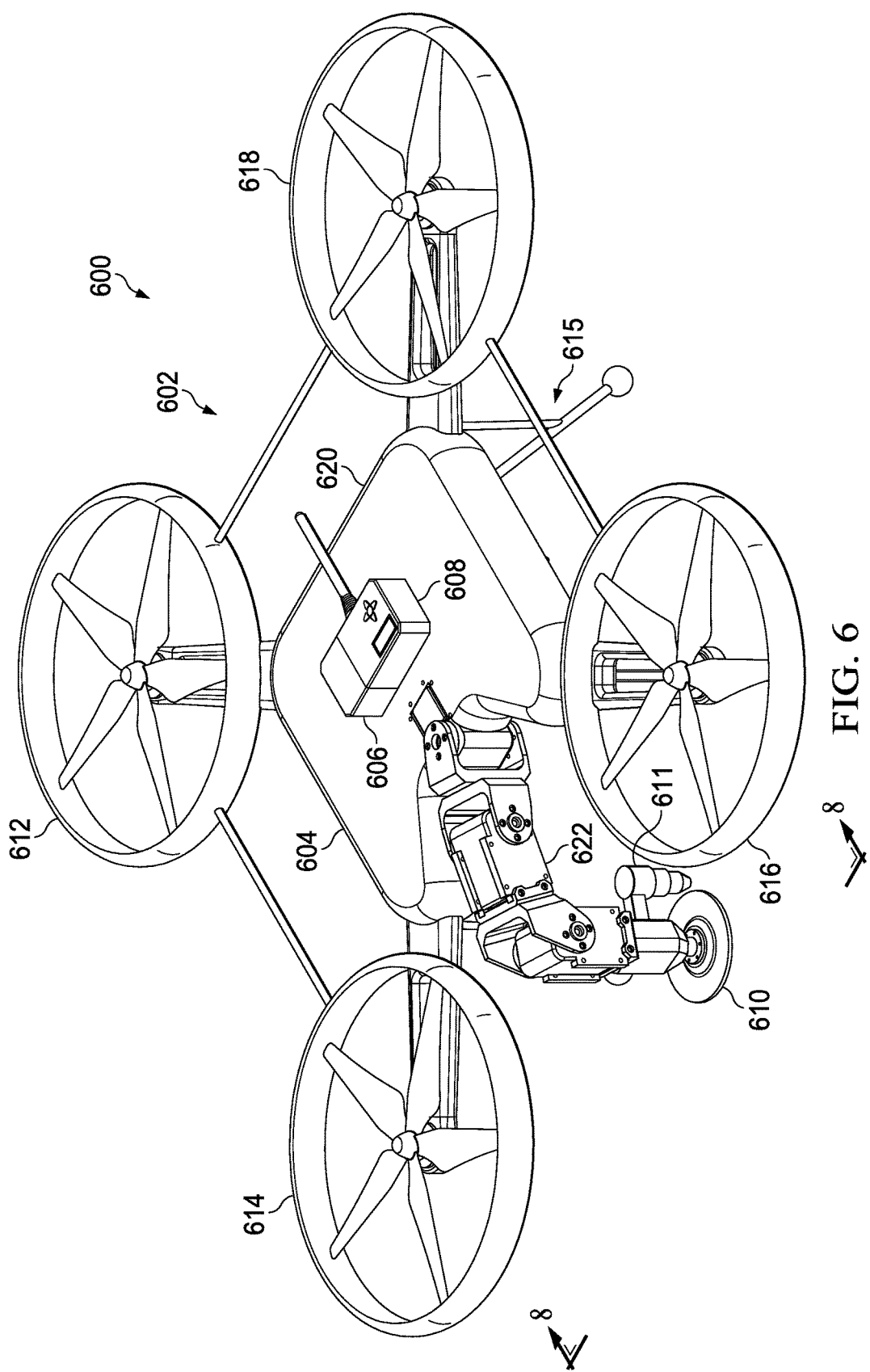
FIG. 6 is an illustration of a mobile inspection unit in the form of an aerial drone in accordance with an illustrative embodiment.

With reference now to FIG. 6, an illustration of a mobile inspection unit in the form of an aerial drone is depicted in accordance with an illustrative embodiment. Mobile inspection unit 600 may be aerial drone 602, such as aerial drone 120 in FIG. 1. As depicted, aerial drone 602 may be an example of a physical implementation for mobile inspection unit 210 shown in block form in FIG. 2.

As depicted in this view, aerial drone 602 may have a number of different components. For example, without limitation, in this view, aerial drone 602 may include automated guided vehicle 604, controller 606, communications system 608, grinder 610, and marker unit 611.

In this illustrative example, aerial drone 602 may have rotor unit 612, rotor unit 614, rotor unit 616, and rotor unit 618 that are associated with body 620. In this manner, aerial drone 602 may move by flying.

Controller 606 may be associated with automated guided vehicle 604. As depicted, controller 606 may be an example of a physical implementation of automated guided vehicle and surface inspection sensor system controller 226 shown in block form in FIG. 2 and may be in communication with automated guided vehicle 604, communications system 408, grinder 610, and other components not shown in this view. Controller 606 may control the operation of these different components to perform inspection and rework operations.

In this illustrative example, communications system 608 may be a wireless communication system. Communications system 608 may provide exchange of information with other devices such as, for example, without limitation, mobile inspection units 208 (not shown) and computer system 250 (not shown).

Grinder 610 may be physically associated with automated guided vehicle 604 through robotic arm 622. As depicted, grinder 610 may be an example of a physical implementation for inconsistency reduction system 224 shown in block form in FIG. 2. As depicted marker unit 611 is also located on robotic arm 622.

In this illustrative example, aerial drone 602 lands and stands using stand structure 615 during grinding. Rotor unit 612, rotor unit 614, rotor unit 616, and rotor unit 618 may be turned off during grinding. Also, rotor unit 612, rotor unit 614, rotor unit 616, and rotor unit 618 may be operated to blow dust (not shown) away.

Figure 7:
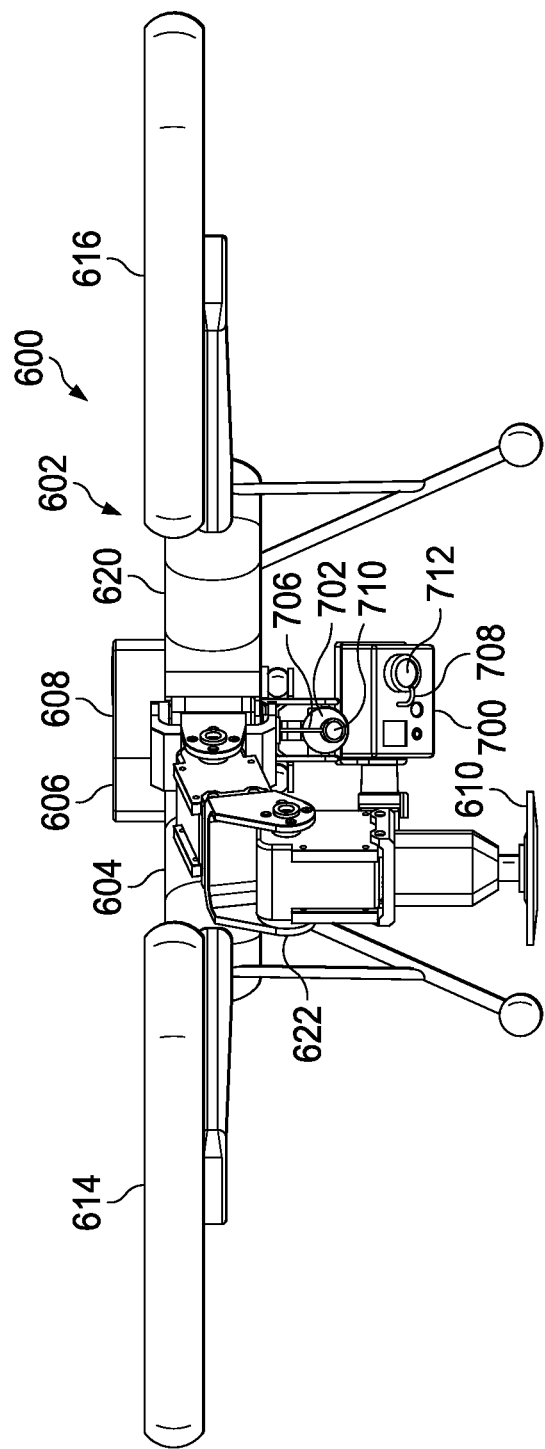
FIG. 7 is an illustration of an aerial drone in accordance with an illustrative embodiment.

With reference next to FIG. 7, an illustration of aerial drone 602 is depicted in accordance with an illustrative embodiment. An illustration of aerial drone 602 is shown taken in the direction of lines 7-7 in FIG. 6.

In this view of aerial drone 602, other components may be seen. As depicted, the components include laser scanner 700 and near infrared camera 702.

Laser scanner 700 may be associated with automated guided vehicle 604. As depicted, laser scanner 700 may be an example of an implementation for surface scanner 302 shown in block form in FIG. 3.

Also, near infrared camera 702 may be seen in this view of aerial drone 602. Near infrared camera 702 may be associated with automated guided vehicle 604. Near infrared camera 702 may be an example of one implementation for material identifier 300 shown in block form in FIG. 3.

In this illustrative example, nozzle 706 may extend from infrared camera 702. Nozzle 708 may extend from laser scanner 700. Nozzle 706 may be configured to blow air (not shown) to remove or prevent dust (not shown) from forming on lens 710 of infrared camera 702. Nozzle 708 may be configured to blow air to remove or prevent dust from forming on lens 712 of laser scanner 700.

As depicted, dust generated during grinding may be cleaned up during other subsequent operations. For example, cleanup of dust may occur after trimming, forming holes, or other operations.

Figure 8:
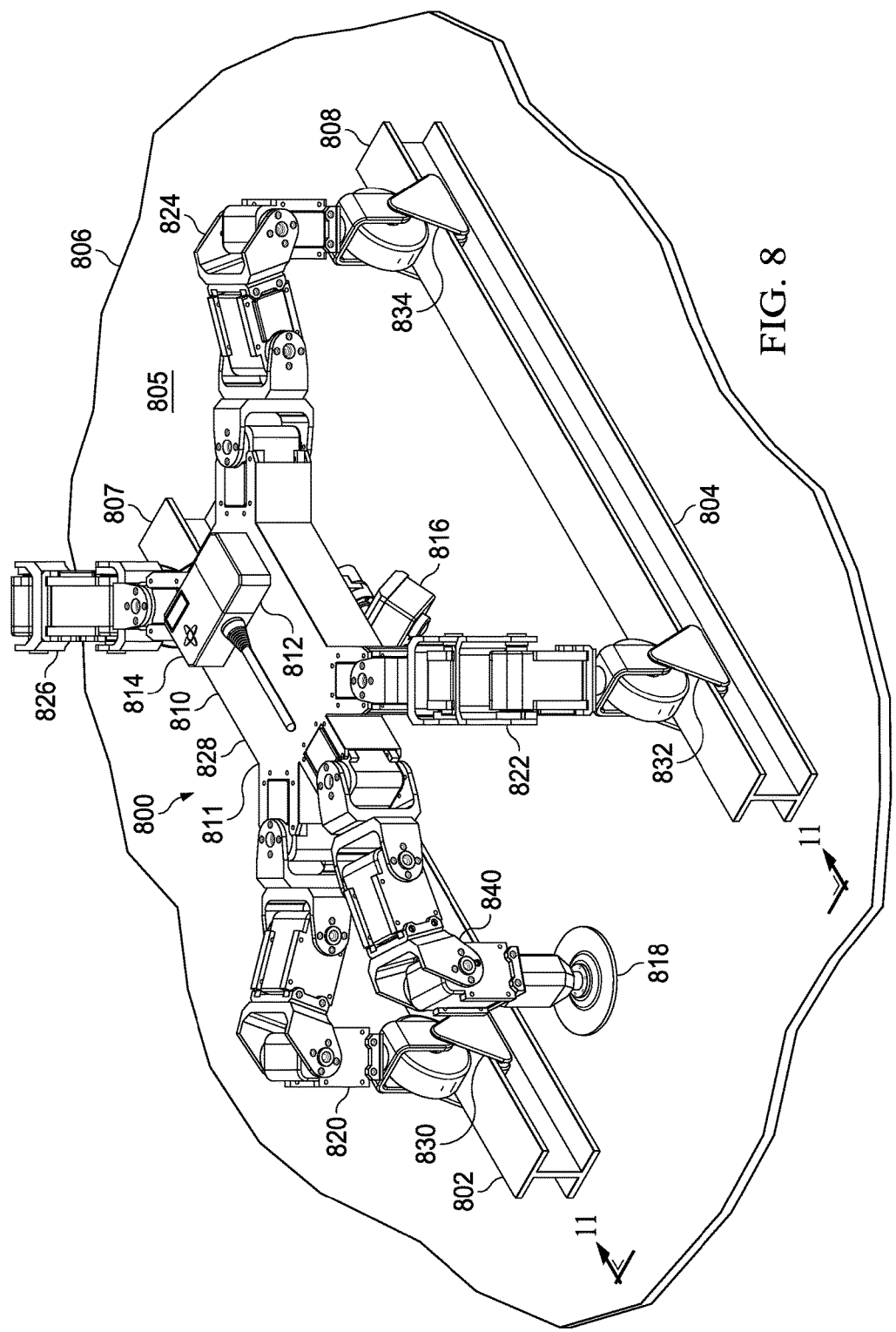
FIG. 8 is an illustration of a mobile inspection unit in accordance with an illustrative embodiment.

With reference now to FIG. 8, an illustration of a mobile inspection unit is depicted in accordance with an illustrative embodiment. Mobile inspection unit 800 may be an example of a physical implementation for mobile inspection unit 210 shown in block form in FIG. 2. In this illustrative example, movement of mobile inspection unit 800 may be guided by structure 802 and structure 804 on surface 805 of composite structure 806. As depicted, structure 802 and structure 804 may be, for example, without limitation, stringer 807 and stringer 808.

As depicted in this view, mobile inspection unit 800 may have a number of different components. For example, without limitation, mobile inspection unit 800 may include automated guided vehicle 810, controller 812, communications system 814, laser scanner 816, and grinder 818.

In this illustrative example, automated guided vehicle 810 may be quadpod 811 having leg 820, leg 822, leg 824, and leg 826 that are associated with body 828. Leg 820 may have motorized wheel system 830, leg 822 may have motorized wheel system 832, and leg 824 may have motorized wheel system 834. Leg 826 also may have a motorized wheel system that is not shown in this view. In this manner, automated guided vehicle may move over surface 805 of composite structure 806.

Controller 812 may be associated with automated guided vehicle 810 and may be an example of a physical implementation of automated guided vehicle and surface inspection sensor system controller 226 shown in block form in FIG. 2. Controller 812 may be in communication with automated guided vehicle 810, communications system 814, laser scanner 816, grinder 818, and other components not shown in this view. Controller 812 may control the operation of these different components to perform inspection and rework of operations.

In this illustrative example, communications system 814 may be a wireless communication system. Communications system 814 may provide exchange of information with other devices such as, for example, without limitation, mobile inspection units 208 (not shown) and computer system 250 (not shown) in FIG. 2.

Laser scanner 816 may be an example of an implementation for surface scanner 302 shown in block form in FIG. 3. Grinder 818 may be associated with automated guided vehicle 810 through robotic arm 840. As depicted, grinder 818 may be an example of a physical implementation for inconsistency reduction system 224 shown in block form in FIG. 2.

Figure 9:
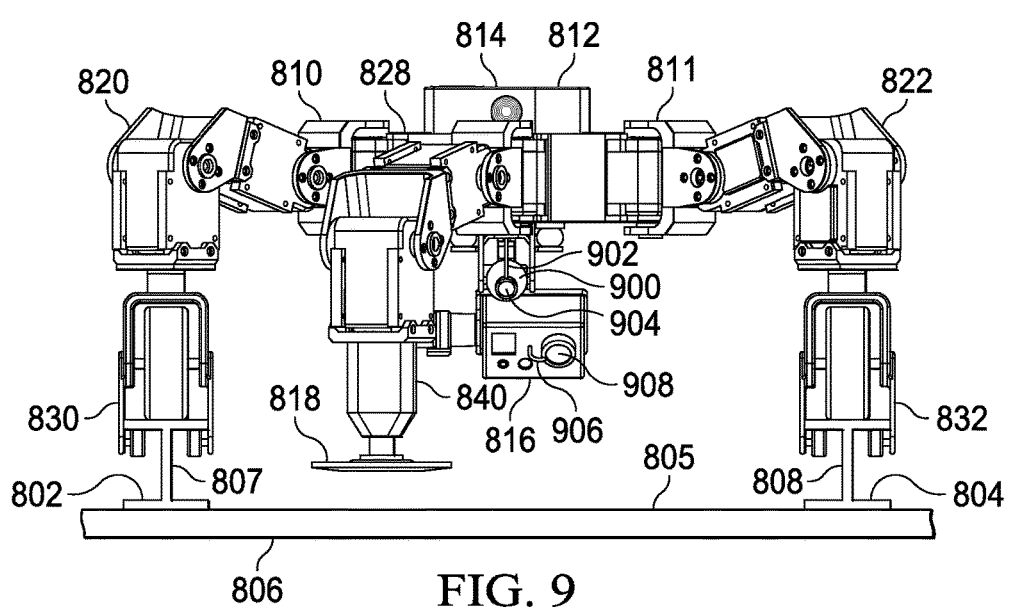
FIG. 9 is another illustration of a mobile inspection unit in accordance with an illustrative embodiment.

Turning next to FIG. 9, another illustration of mobile inspection unit 800 is depicted in accordance with an illustrative embodiment. In this figure, mobile inspection unit 800 is shown in a view in the direction of lines 9-9 in FIG. 8.

In this view of mobile inspection unit 800, near infrared (NIR) camera 900 may be seen. Near infrared (NIR) camera 900 may be associated with automated guided vehicle 810. Near infrared camera 900 may be an example of one implementation for material identifier 300 shown in block form in FIG. 3.

In this view, nozzle 902 may be associated with infrared camera 900. Nozzle 902 may blow air (not shown) in a manner that prevents dust (not shown) from forming on lens 904 or removes dust from lens 904 on infrared camera 900. Nozzle 906 may be located on laser scanner 816. Nozzle 906 may blow air in a manner that prevents dust from forming on lens 908 or removes dust on lens 904

Figure 10:
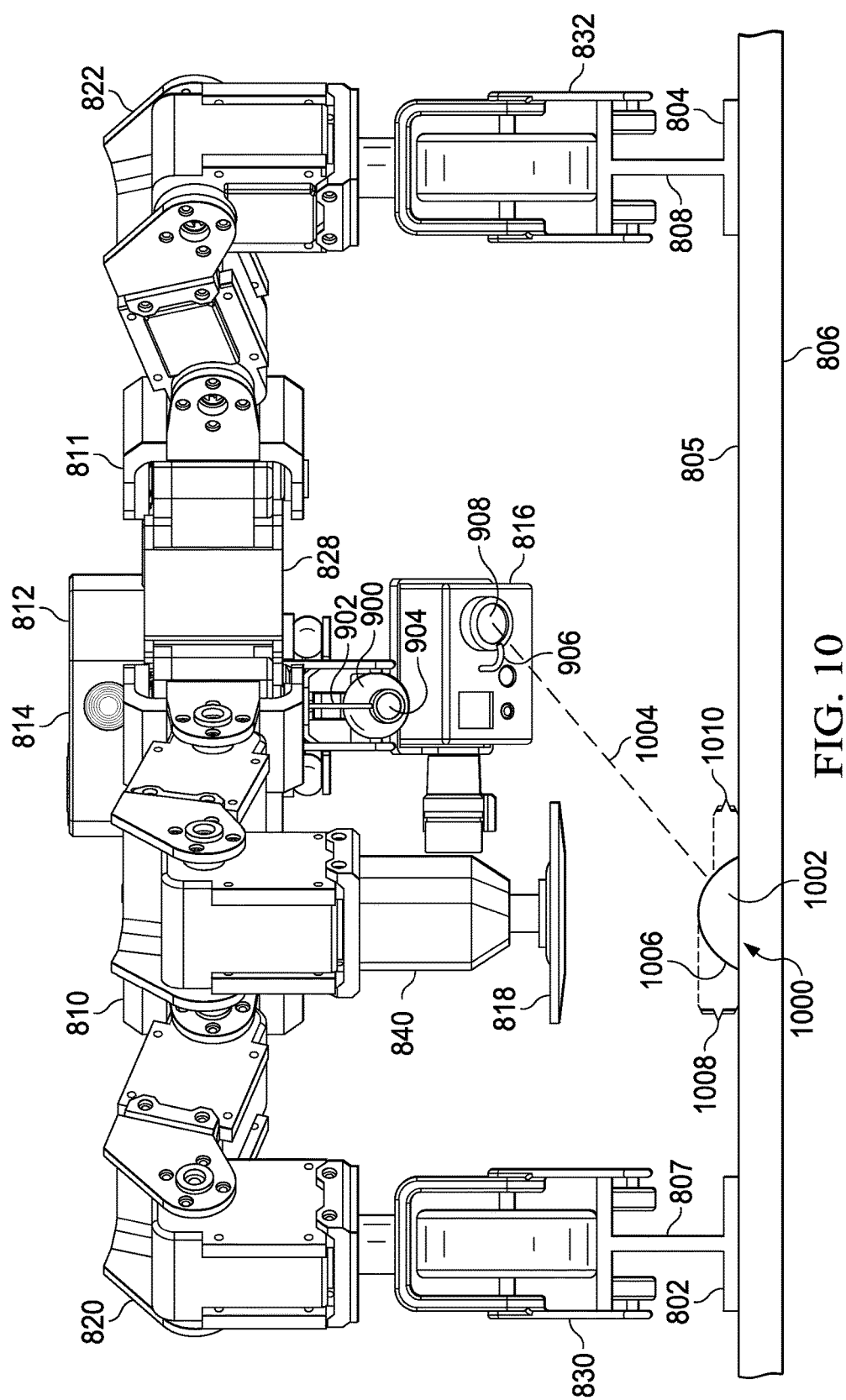
FIG. 10 is an illustration of a mobile inspection unit over a location in accordance with an illustrative embodiment.
Figure 11:
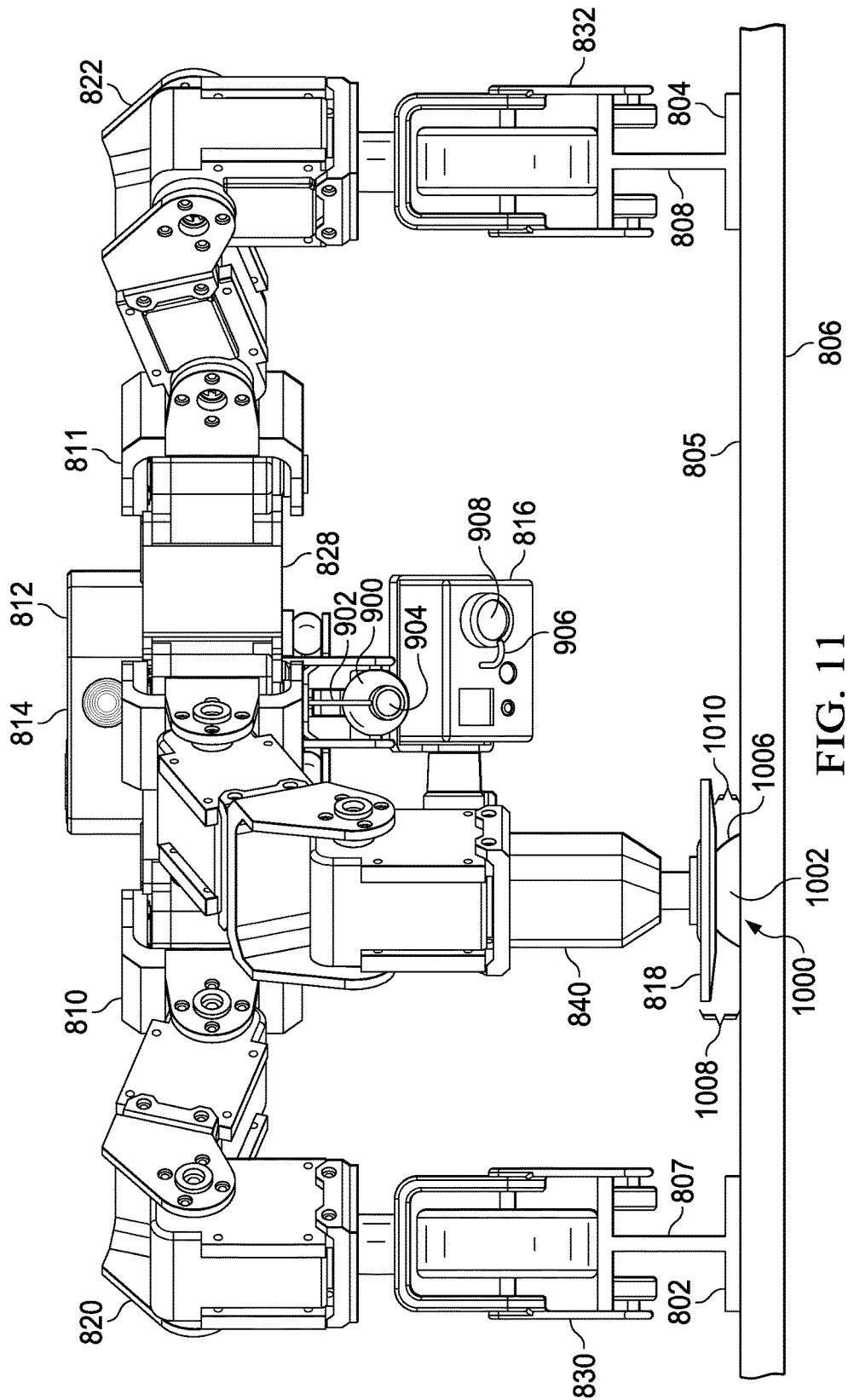
FIG. 11 is an illustration of a mobile inspection unit reducing a resin ridge in accordance with an illustrative embodiment.

FIGS. 10-11 illustrate reducing a resin ridge in accordance with an illustrative embodiment. In FIG. 10, an illustration of a mobile inspection unit 800 is depicted over location 1000 in accordance with an illustrative embodiment. In this example, resin 1002 may be at location 1000.

As depicted, mobile inspection unit 800 has moved to location 1000 along stringer 807 and stringer 808. In this illustrative example, near infrared camera 900, controlled by controller 812, may identify resin 1002 at location 1000. Laser scanner 816 emits laser beam 1004 to scan surface 805 of composite structure 806.

In this manner, controller 812 may determine whether resin 1002 is resin ridge 1006 and whether resin ridge 1006 has height 1008 greater than desired height 1010. For example, without limitation, near infrared camera 900 may allow controller 812 to identify where resin 1002 is located and whether resin 1002 is considered to be resin rich. Laser scanner 816 may allow controller 812 to identify a profile for surface 805. These two pieces of data may be used to determine whether resin 1002 is resin ridge 1006.

Next, in FIG. 11, an illustration of a mobile inspection unit reducing a resin ridge is depicted in accordance with an illustrative embodiment. In this figure, grinder 818 has been moved over resin ridge 1006 and may be operated to reduce resin ridge 1006 by grinding resin ridge 1006.

The amount of grinding performed by grinder 818 may be incremental. An inspection may be made after some of resin ridge 1006 is removed. For example, without limitation, near infrared camera 900 and laser scanner 816 may be operated by controller 812 to determine whether height 1008 of resin ridge 1006 is desired height 1010. In other words, resin ridge may be ground from being out of tolerance 238 to being within tolerance 238.

The illustrations of mobile inspection unit 400 in FIGS. 4-5, mobile inspection unit 600 in FIGS. 6-7, and mobile inspection unit 800 in FIGS. 8-11 are provided as examples of implementations for mobile inspection unit 210 in FIG. 2 and are not meant to limit the manner in which mobile inspection unit 210 may be implemented in an illustrative example.

For example, without limitation, mobile inspection unit 800 may be guided on structure 802 and structure 804 taking the form of rails on a rail system that may be attached to composite structure 806. In still another example, mobile inspection unit 210 may be implemented in which automated guided vehicle 404 uses tracks, suction cups, or other locomotion mechanisms in addition to or in place of legs, rotor units, or motorized wheel systems. As another example, stringer 807 and stringer 808 have an I beam cross section. In other illustrative examples stringer 807 and stringer 808 may have other types of cross sections, such as a T cross section, an L cross section, a C cross section, a J cross section, a Z cross section, a hat cross section, or some other suitable type of cross section for stringer 807 and stringer 808.

As also illustrated, mobile inspection unit has have marker unit 413 and mobile inspection unit 600 has marker unit 611. Mobile inspection unit 800 does not include a marker unit in the illustrative examples.

Figure 12:
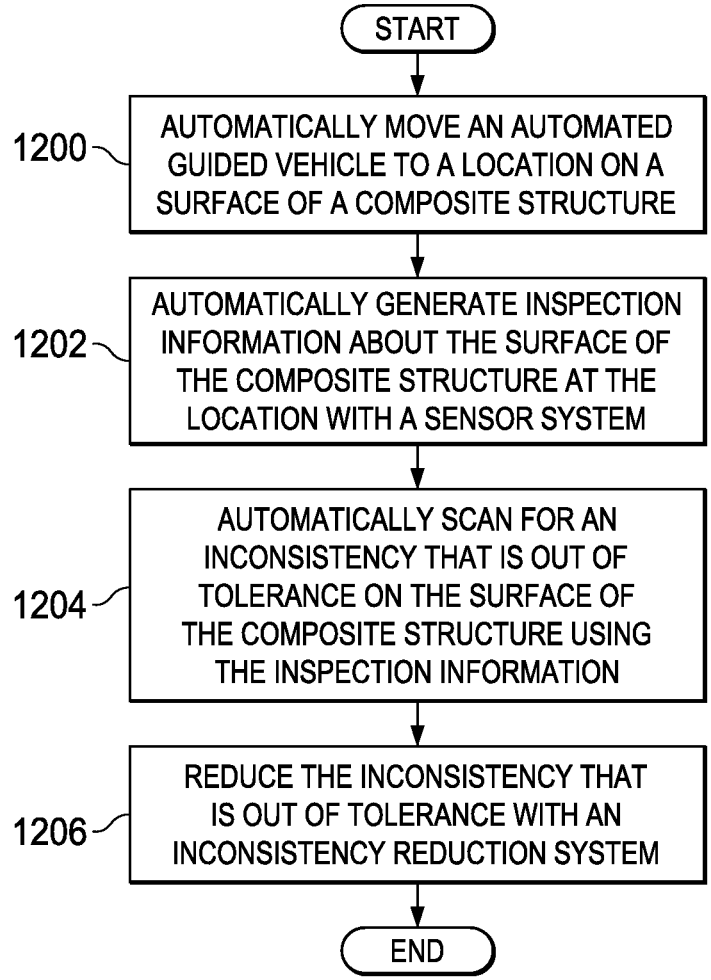
FIG. 12 is an illustration of a flowchart of a process for reducing an undesired inconsistency on a surface of the composite structure in accordance with an illustrative embodiment.

With reference next to FIG. 12, an illustration of a flowchart of a process for reducing an undesired inconsistency on a surface of the composite structure is depicted in accordance with an illustrative embodiment. The process illustrated in this figure may be implemented in composite manufacturing environment 200 shown in block form in FIG. 2. For example, without limitation, the process may be implemented using mobile inspection unit 210 in structure management system 202 in FIG. 2.

The process may begin by automatically moving automated guided vehicle 220 to location 216 on surface 212 of composite structure 204 (operation 1200). The process may automatically generate inspection information 228 about surface 212 of composite structure 204 at location 216 with sensor system 222 (operation 1202). The process may automatically scan for inconsistency 214 that is out of tolerance 238 on surface 212 of composite structure 204 using inspection information 228 (operation 1204).

The process may automatically reduce inconsistency 214 that is out of tolerance 238 with inconsistency reduction system 224 (operation 1206) with the process terminating thereafter. This process may enable an efficient reduction of inconsistency 214 from out of tolerance 238 to within tolerance 238.

Figure 13:
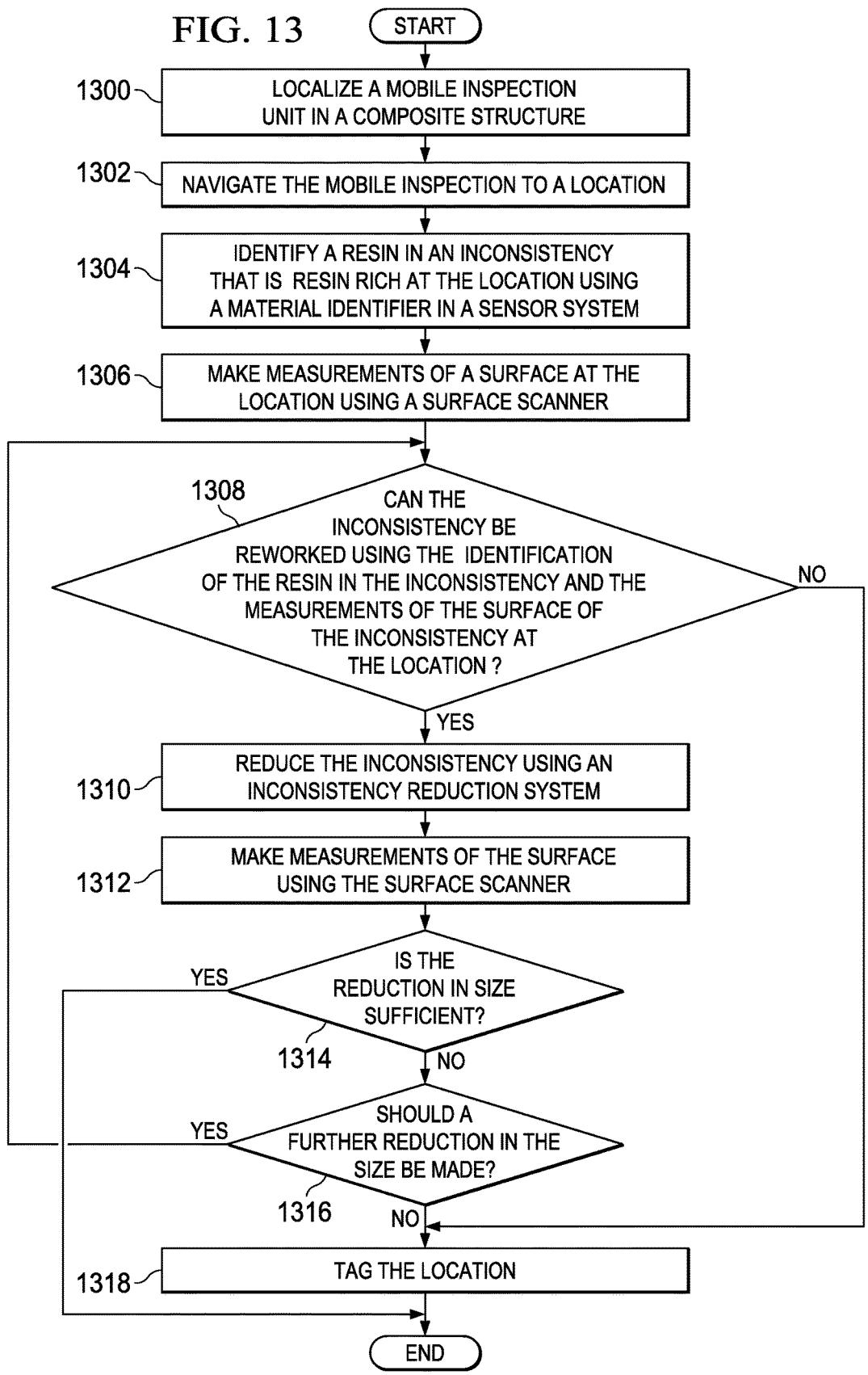
FIG. 13 is a more detailed illustration of a flowchart of a process for reducing an undesired inconsistency on a surface of the composite structure in accordance with an illustrative embodiment.

With reference now to FIG. 13, a more detailed illustration of a flowchart of a process for reducing an undesired inconsistency on a surface of the composite structure is depicted in accordance with an illustrative embodiment. The process illustrated in this figure may be implemented in composite manufacturing environment 200 shown in block form in FIG. 2. In particular, the process may be implemented using mobile inspection unit 210 in structure management system 202 in FIG. 2.

The process may begin by localizing mobile inspection unit 210 on composite structure 204 (operation 1300). In operation 1300, mobile inspection unit 210 may identify where mobile inspection unit 210 is located on composite structure 204. The process may then navigate mobile inspection unit 210 to location 216 (operation 1302). In this illustrative example, location 216 may be, for example, without limitation, a caul area.

In this illustrative example, location 216 may be identified in a number different ways. For example, without limitation, location 216 may be identified using at least one of a pen mark, paint, a sticker, tape, a structure, a radio frequency identifier (RFID) chip a stringer, a rib, or some other landmark or indicator at or adjacent to location 216.

The process may then identify a resin 304 in inconsistency 214 that is resin rich at location 216 using material identifier 300 in sensor system 222 (operation 1304). The process also may make measurements of surface 212 at location 216 using surface scanner 302 (operation 1306). As depicted, operation 1304 and operation 1306 may scan for inconsistency 214 that is out of tolerance 238. The scanning may be performed while mobile inspection unit 210 is stationary at location 216, moving with respect to location 216, or some combination thereof.

The process may determine whether inconsistency 214 can be reworked using the identification of resin 304 in inconsistency 214 and measurements of surface 212 of inconsistency 214 at location 216 (operation 1308). For example, without limitation, the measurements of surface 212 of inconsistency 214 in operation 1308 may be used to determine whether resin 304 in inconsistency 214 is out of tolerance 238 by being greater than desired height 312. If inconsistency 214 is greater than desired height 312, then inconsistency 214 may be resin ridge 323, which can be reworked. If inconsistency 214 can be reworked, inconsistency 214 may be reduced using inconsistency reduction system 224 (operation 1310).

In operation 1310, inconsistency 214 may be reduced by sanding, grinding, or some other suitable reduction process to reduce size 240 of inconsistency 214. The reduction in size 240 of inconsistency 214 may occur through the removal of resin 304 in this illustrative example. This reduction may be some predetermined amount and may not result in a complete reduction of inconsistency 214. The predetermined amount may be one selected that reduces a likelihood that removal of resin 304 may also cause at least one of removal or exposure of fibers 322.

The process may then make measurements of the surface 212 using surface scanner 302 (operation 1312). A determination may be made as to whether the reduction in size 240 is sufficient (operation 1314). In this manner, operation 1314 may determine whether resin ridge 323 is within tolerance 238 or out of tolerance 238.

Although this determination is made after resin 304 is removed from resin ridge 323 in this depicted example, operation 1314 may be performed at any time in the process. For example, the determination in operation 1314 may be made while reduction of resin ridge 323 is made in addition to or in place of determining whether resin ridge 323 is within tolerance 238 after reducing resin ridge 323.

If the reduction in size 240 is such that resin ridge 323 is within tolerance 238 in operation 1314, the process may terminate. If the reduction in size 240 is insufficient, a determination may be made as to whether a further reduction in size 240 should be made (operation 1316). Operation 1316 may be performed to determine whether fibers 322 will be exposed with further reduction of resin ridge 323 when resin ridge 323 is out of tolerance 238. If a further reduction can be made, the process may return to operation 1308. In this manner, inconsistency 214 may be reduced incrementally in a manner that avoids undesired results, such as sanding or grinding fibers 322.

With reference again to operation 1316, if a further reduction should not be made, location 216 may be tagged (operation 1318) with the process terminating thereafter. In this manner, location 216 may be further examined to determine whether other types of rework may be performed or if composite structure 204 may need to be rejected. Further, with reference again to operation 1308, if inconsistency 214 should not be reduced, the process also may proceed to operation 1318.

Figure 14:
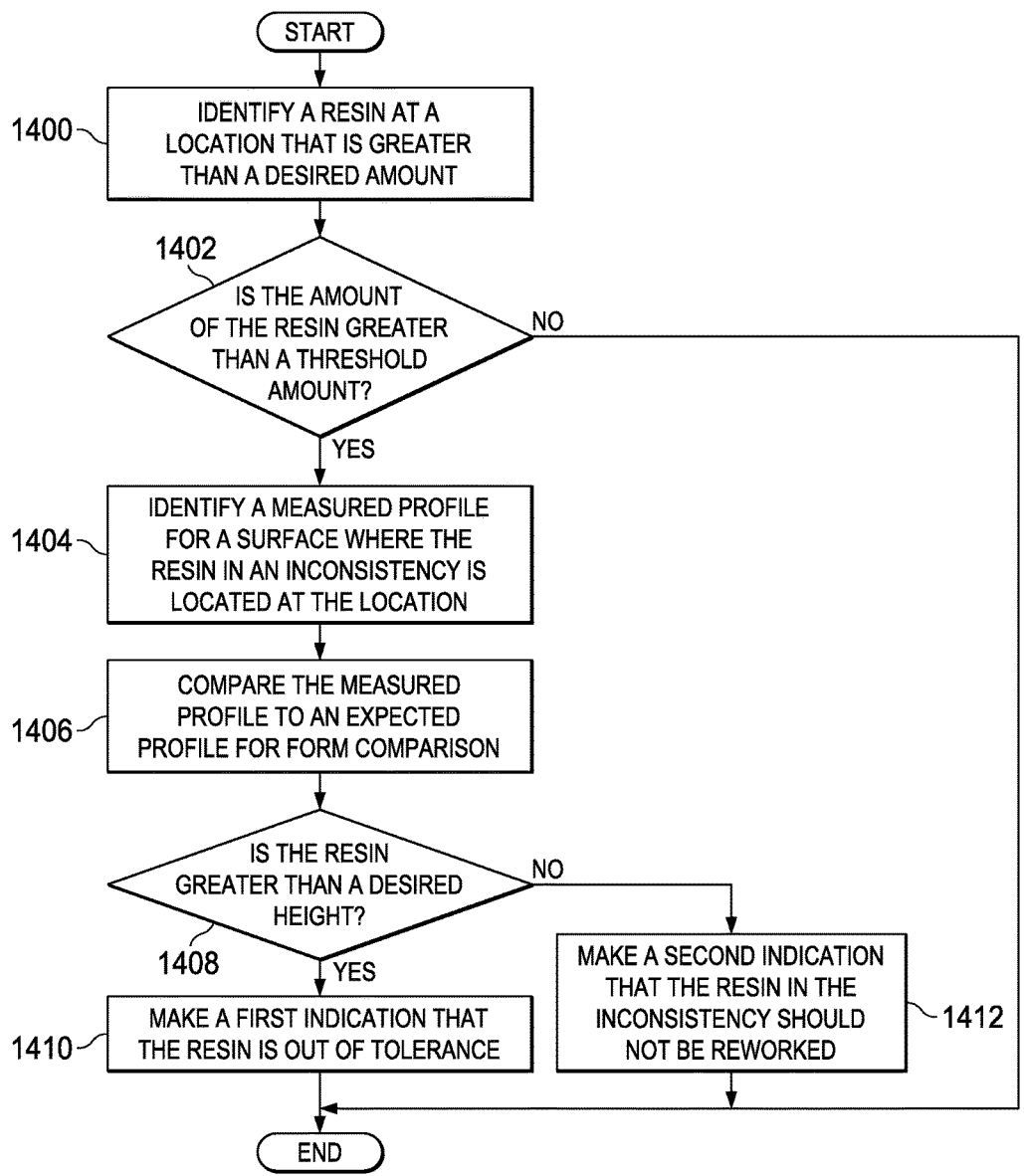
FIG. 14 is an illustration of a flowchart of a process for identifying an undesired inconsistency for reduction in accordance with an illustrative embodiment.

With reference next to FIG. 14, an illustration of a flowchart of a process for identifying an undesired inconsistency for reduction is depicted in accordance with an illustrative embodiment. The process illustrated in FIG. 14 may be implemented in composite manufacturing environment 200 shown in block form in FIG. 2.

In particular, the process may be implemented using automated guided vehicle and surface inspection sensor system controller 226 in structure management system 202 FIG. 2. The process in automated guided vehicle and surface inspection sensor system controller 226 may use inspection information 228 for location 216 on surface 212 of composite structure 204. The process illustrated in FIG. 14 is an example of one implementation for operation 1308 in FIG. 13.

The process may begin by identifying resin 304 at location 216 that is greater than a desired amount (operation 1400). In other words, operation 1400 may determine whether resin 304 at location 216 has a concentration at location 216 that is greater than some tolerance. For example, the process may determine whether resin 304 at location 216 is resin rich. The identification may be made by material identifier 300, which may be a near infrared (NIR) camera. A determination may be made as to whether the amount of resin 304 is greater than threshold amount 310 (operation 1402).

If the amount of resin 304 is greater than threshold amount 310, resin 304 may be part of inconsistency 214 that is out of tolerance 238. Measured profile 306 may be identified for surface 212 where resin 304 in inconsistency 214 is located at location 216 (operation 1404). As depicted, measured profile 306 may be identified from inspection information 228 generated by surface scanner 302.

As depicted, measure profile 306 may be compared to expected profile 314 to form comparison 316 (operation 1406). A determination may be made as to whether resin 304 is greater than desired height 312 (operation 1408). Operation 1408 may be used to determine whether resin 304 in resin ridge 323 for inconsistency 214 is out of tolerance 238.

If resin 304 in inconsistency 214 is greater than desired height 312, a first indication may be made that resin 304 in inconsistency 214 is out of tolerance 238 (operation 1410) with the process terminating thereafter. Otherwise, a second indication may be made that resin 304 in inconsistency 214 should not be reworked (operation 1414) with the process terminating thereafter.

In this case, resin 304 is not greater than desired height 312. In operation 1414, resin 304 may be under surface 212 and may not be removed in a manner that composite structure 204 maintains desired performance. In this example, although inconsistency 214 may be out of tolerance 238, location 216 of inconsistency 214 is under surface 212 and may make reworking inconsistency 214 by grinding impractical. As a result, other inspections or rework may be needed.

With reference again to operation 1402, if the amount of resin 304 is not greater than the threshold amount 310, the process also may proceed to operation 1414. In this case, resin 304 may not need to be removed. The process in FIG. 14 may be repeated any number of times for process inspection information 228 for any number of locations 256 on surface 212 of composite structure 204.

Figure 15:
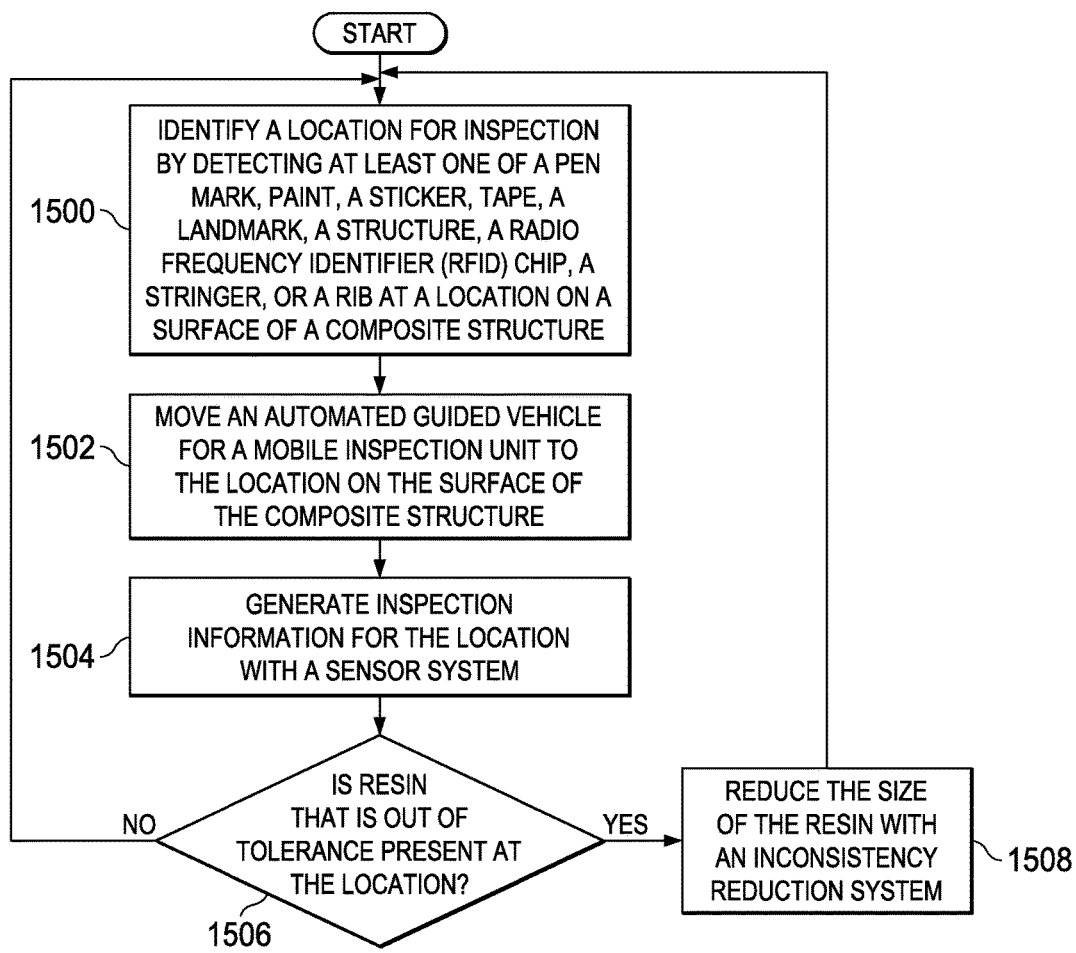
FIG. 15 is an illustration of a flowchart of a process for reducing a resin on a surface of a composite structure in accordance with an illustrative embodiment.

Turning now to FIG. 15, an illustration of a flowchart of a process for reducing resin 304 on surface 212 of composite structure 204 is depicted in accordance with an illustrative embodiment. The process illustrated in FIG. 15 may be implemented in composite manufacturing environment 200 in FIG. 2. The process may be implemented using mobile inspection unit 210 in FIG. 2.

The process may begin by identifying location 216 for inspection by detecting at least one of a pen mark, paint, a sticker, tape, a landmark, a structure, a radio frequency identifier (RFID) chip, a stringer, or a rib at location 216 on surface 212 of composite structure 204 (operation 1500). The process may move automated guided vehicle 404 for mobile inspection unit 210 to location 216 on surface 212 of composite structure 204 (operation 1502). In operation 1502, automated guided vehicle 404 may move over surface 212 of composite structure 204 by at least one of moving over surface 212 without contact with surface 212 or moving over surface 212 while in contact with surface 212. Automated guided vehicle 220, in this example, may be selected from one of an autonomous crawler, an aerial drone, an unmanned ground vehicle, and an unmanned aerial vehicle. Also, automated guided vehicle and surface inspection sensor system controller 226 autonomously controls movement of automated guided vehicle 220 on surface 212 of composite structure 204.

The process may generate inspection information 228 for location 216 with sensor system 222 (operation 1504). Sensor system 222 may be selected from at least one of a near infrared imaging camera, a laser scanner, a visible light camera, a stereoscopic camera, a tactile sensor system, a physical probe, a micrometrology probe, a chromatic white light sensor, or a video camera.

The process also may determine whether resin 304 is present at location 216 that is out of tolerance 238 using inspection information 228 (operation 1506). In operation 1506, the process may, for example, without limitation, identify location 216 of resin 304 within inconsistency 214 that is out of tolerance 238 using material identifier 300; identify measured profile 306 of surface 212 at location 216 using surface scanner 302; and determine whether size 240 of resin 304 can be reduced to be within tolerance 238 without damaging fibers 322. In other words, the process may determine whether resin 304 in inconsistency 214 that is out of tolerance 238 is in the form of resin ridge 323 or embedded under surface 212.

With reference again to operation 1506, when resin 304 in inconsistency 214 is out of tolerance 238, the process may reduce size 240 of resin 304 with inconsistency reduction system 224 when inconsistency 214 is out of tolerance 238 until inconsistency 214 is within tolerance 238 (operation 1508) with the process then returning to operation 1500. With reference again to operation 1506, if resin 214 is within tolerance 238, the process also returns to operation 1500 as described above. As a result, an efficient reduction of undesired inconsistency 338 may be enabled.

Figure 16:
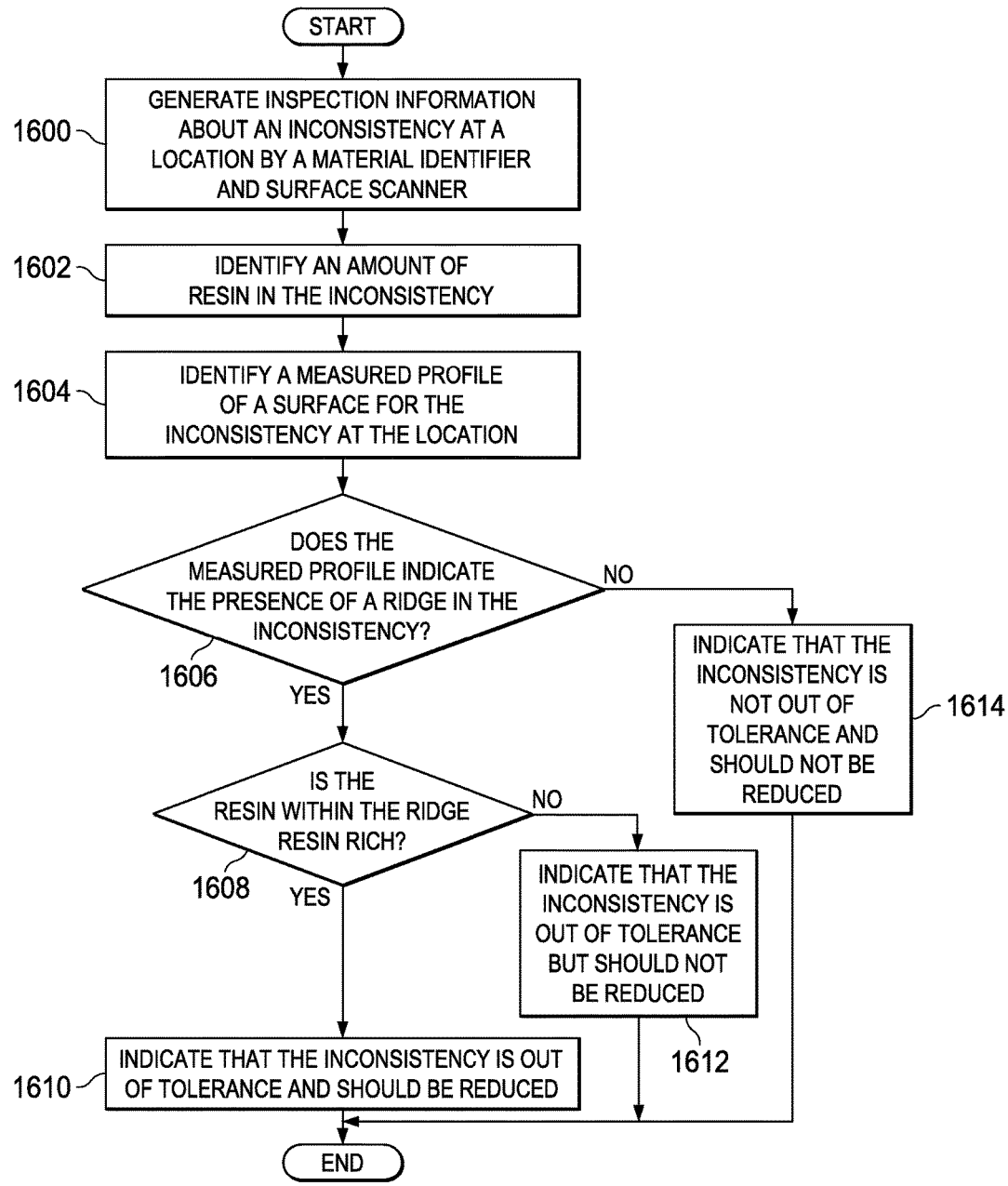
FIG. 16 is an illustration of a flowchart of a process for determining whether an inconsistency is out of tolerance and should be reduced in accordance with an illustrative embodiment.

Turning next to FIG. 16, an illustration of a flowchart of a process for determining whether an inconsistency is out of tolerance and should be reduced is depicted in accordance with an illustrative embodiment. The process illustrated in FIG. 16 may be implemented in mobile inspection unit 210.

The process may begin with material identifier 300 and surface scanner 302 generating inspection information 228 about inconsistency 214 at location 216 (operation 1600). The process may identify amount 305 of resin 304 in inconsistency 214 (operation 1602). The process may also identify a measured profile of surface 212 for inconsistency 214 at location 216 (operation 1604).

The process may determine whether measured profile 306 indicates the presence of a ridge in inconsistency 214 (operation 1606). The determination in operation 1606 may be performed by comparing measured profile 306 with expected profile 314. If a ridge is present, then surface 212 does not have a desired profile in this example.

If a ridge is present, the process may determine whether resin 304 in inconsistency 214 within the ridge is resin rich (operation 1608). In operation 1608, if resin 304 is resin rich, the ridge may be resin ridge 323. In this case, the process may indicate that inconsistency 214 is out of tolerance and should be reduced (operation 1610) with the process determining thereafter.

With reference again operation 1608, if resin 304 in inconsistency 214 within ridge is not resin rich, the process may indicate that inconsistency 204 is out of tolerance but should not be reduced (operation 1612) with the process terminating thereafter. With reference again to operation 1606, if the presence of a ridge is not detected, the process may indicate that the inconsistency is not out of tolerance and should not be reduced (operation 1614) with the process terminating thereafter.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step. For example, without limitation, one or more of the blocks may be implemented as program code, in hardware, or a combination of the program code and hardware. When implemented in hardware, the hardware may, for example, without limitation, take the form of integrated circuits that are manufactured or configured to perform one or more operations in the flowcharts or block diagrams. When implemented as a combination of program code and hardware, the implementation may take the form of firmware.

In some alternative implementations of an illustrative embodiment, the function or functions noted in the blocks may occur out of the order noted in the figures. For example, without limitation, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

For example, in operation 1606, if a ridge is not detected, the process may still determine whether the resin 304 is resin rich. In this case, if resin 304 is resin rich and a ridge is not present, the process may indicate the presence of pocket 324 of resin 304.

Figure 17:
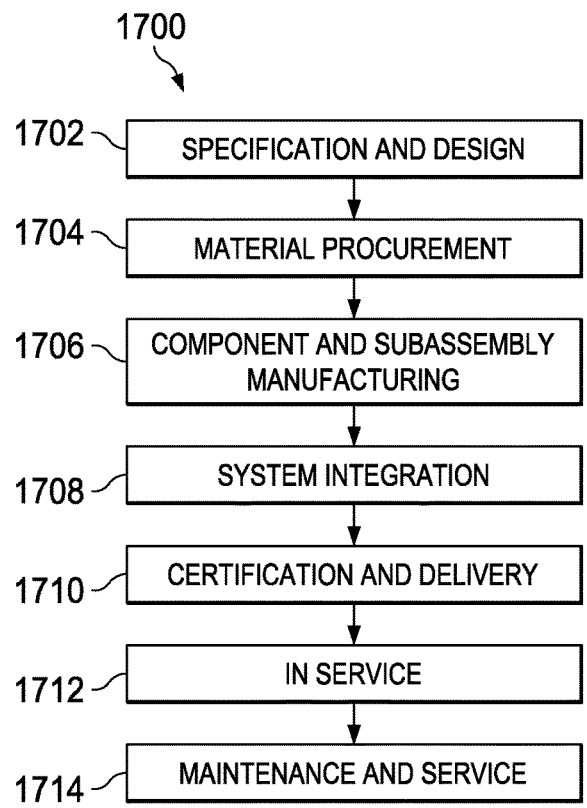
FIG. 17 is an illustration of an aircraft manufacturing and service method in accordance with an illustrative embodiment.
Figure 18:
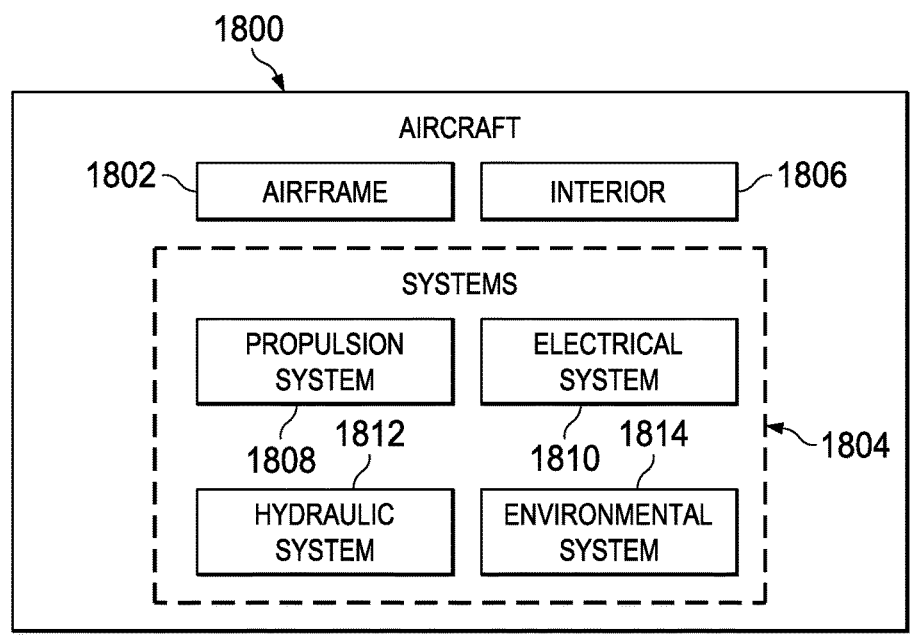
FIG. 18 is an illustration of an aircraft manufactured using an aircraft manufacturing and service method in accordance with an illustrative embodiment.

Illustrative embodiments of the disclosure may be described in the context of an aircraft manufacturing and service method 1700 as shown in FIG. 17 and an aircraft 1800 as shown in FIG. 18. During pre-production, the aircraft manufacturing and service method 1700 may include specification and design 1702 of aircraft 1700 and material procurement 1704. During production, component and subassembly manufacturing 1706 and system integration 1708 of aircraft 1800 takes place. Thereafter, aircraft 1800 may go through certification and delivery 1710 in order to be placed in service 1612. While in service 1712 by a customer, aircraft 1800 is scheduled for routine maintenance and service 1714 (which may also include modification, reconfiguration, refurbishment, and so on).

Each of the processes of aircraft manufacturing and service method 1700 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 18, the aircraft 1800 produced by the aircraft manufacturing and service method 1700 may include an airframe 1802 with a plurality of systems 1804 and interior 1806. Examples of high-level systems 1804 include one or more of propulsion system 1808, electrical system 1810, hydraulic system 1812, and environmental system 1814. Any number of other systems may be included. Although an aerospace example is shown, the principles of the invention may be applied to other industries, such as the automotive industry.

Apparatus and methods embodied herein may be employed during any one or more of the stages of the aircraft manufacturing and service method 1700. For example, components or subassemblies corresponding to the production process in component and subassembly manufacturing 1706 may be fabricated or manufactured in a manner similar to components or subassemblies produced while the aircraft 1800 is in service. Also, one or more apparatus embodiments, method embodiments, or a combination thereof may be utilized during the production stages, component and subassembly manufacturing 1706 and system integration 1708, to reduce inconsistencies such as resin ridges that are out of tolerance. Using an illustrative embodiment may substantially expedite assembly, or reduce the cost, of aircraft 1800. Similarly, one or more apparatus embodiments, method embodiments, or a combination thereof may be utilized to reduce inconsistencies that are out of tolerance while aircraft 1800 is in maintenance and service 1714.

Thus, the illustrative examples may provide a method and apparatus for reworking composite structure 204. In an illustrative example, mobile inspection unit 210 may solve the technical problem with the increased time, increased expense, or both the increased time and expense occurring with reworking or discarding composite structures. Further reductions in time, expense, or expense and time may occur when mobile inspection units 208 perform inspections on composite structure 204 cooperatively as swarm 258.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, without limitation, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
   an automated guided vehicle, comprising a crawler, that moves on a surface of a composite structure during operation of the apparatus to inspect the composite structure;
   a surface inspection sensor system connected to the automated guided vehicle;
   an automated guided vehicle and surface inspection sensor system controller in communication with the automated guided vehicle and the surface inspection sensor system;
   wherein the surface inspection sensor system is configured to generate inspection information about the surface of the composite structure during the operation of the apparatus, and the automated guided vehicle and surface inspection sensor system controller is configured to autonomously control movement of the automated guided vehicle on the surface of the composite structure, receive the inspection information from the surface inspection sensor system, and scan for an inconsistency that is out of tolerance on the surface of the composite structure using the inspection information;
   wherein in being configured to scan for the inconsistency that is out of tolerance, the automated guided vehicle and surface inspection sensor system controller is further configured to identify a measured profile from inspection information, compare the measured profile with an expected profile to form a comparison, determine whether the inconsistency is out of tolerance and should be reduced based on the comparison, and identify how much to reduce the inconsistency from the comparison when the inconsistency is out of tolerance and should be reduced; and
   an inconsistency reduction system connected to the automated guided vehicle, wherein the automated guided vehicle and surface inspection sensor system controller is configured to control the inconsistency reduction system to reduce the inconsistency that is identified as being out of tolerance.

* * * * *